(12) United States Patent
Hegde et al.

(10) Patent No.: US 7,846,425 B2
(45) Date of Patent: *Dec. 7, 2010

(54) PROCESS FOR THE PREPARATION OF SEVELAMER HYDROCHLORIDE AND FORMULATION THEREOF

(75) Inventors: Deepak Anant Hegde, Thane (IN); Varsha Shashank Choudhary, Mumbai (IN); Yogesh Sharad Bhide, Pune (IN)

(73) Assignee: USV, Ltd., Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 12/620,931

(22) Filed: Nov. 18, 2009

(65) Prior Publication Data

US 2010/0092421 A1    Apr. 15, 2010

Related U.S. Application Data

(63) Continuation of application No. 12/377,129, filed as application No. PCT/IN2007/000387 on Aug. 31, 2007.

(30) Foreign Application Priority Data

Sep. 1, 2006    (IN) ................... 1402/MUM/2006

(51) Int. Cl.
*A61K 31/785*    (2006.01)
*A61P 13/12*    (2006.01)
*C08G 61/02*    (2006.01)

(52) U.S. Cl. .................................. 424/78.35; 528/393

(58) Field of Classification Search .............. 424/78.35; 528/393
See application file for complete search history.

(56) References Cited

U.S. PATENT DOCUMENTS

| | | | |
|---|---|---|---|
| 4,605,701 A | 8/1986 | Harada et al. | |
| 5,275,824 A | 1/1994 | Carli et al. | |
| 5,490,987 A | 2/1996 | Shen et al. | |
| 5,496,545 A | 3/1996 | Holmes-Farley et al. | |
| 6,121,411 A | 9/2000 | Sartori et al. | |

(Continued)

FOREIGN PATENT DOCUMENTS

EP    1304104 B1    4/2003

(Continued)

OTHER PUBLICATIONS

Foreign Priority document 1402/MUM/2006 (filing date Sep. 1, 2006), retrieved from the WIPO site, pp. 1-22.*

(Continued)

*Primary Examiner*—Robert A Wax
*Assistant Examiner*—Aradhana Sasan
(74) *Attorney, Agent, or Firm*—Pharmaceutical Patent Atty's, LLC

(57) ABSTRACT

Disclosed herein is an improved process for preparation of Sevelamer hydrochloride having phosphate binding capacity of 4.7 to 6.4 mmol/g. Further, the invention discloses Sevelamer hydrochloride compositions and a novel process for preparation of said compositions comprising high shear non-aqueous granulation.

17 Claims, 15 Drawing Sheets

U.S. PATENT DOCUMENTS

| | | |
|---|---|---|
| 6,362,266 B1 | 3/2002 | Buchholz et al. |
| 6,383,518 B1 | 5/2002 | Matsuda et al. |
| 6,525,113 B2 | 2/2003 | Klix et al. |
| 6,600,011 B2 | 7/2003 | McDonnell et al. |
| 6,733,780 B1 | 5/2004 | Tyler et al. |
| 6,756,364 B2 | 6/2004 | Barbier et al. |
| 7,229,613 B2 | 6/2007 | Burke et al. |
| 7,381,424 B2 | 6/2008 | MacGregor |
| 7,388,056 B2 | 6/2008 | Gopalkrishna et al. |
| 2002/0054903 A1 | 5/2002 | Tyler et al. |
| 2002/0119193 A1* | 8/2002 | Le et al. ............. 424/465 |
| 2005/0131138 A1 | 6/2005 | Connor et al. |
| 2007/0027213 A1* | 2/2007 | Oberegger et al. ...... 514/563 |
| 2007/0190020 A1* | 8/2007 | Hrakovsky et al. ...... 424/78.27 |
| 2007/0190135 A1 | 8/2007 | Matsuda et al. |
| 2009/0280178 A1* | 11/2009 | Hedge et al. ............. 424/474 |

FOREIGN PATENT DOCUMENTS

| | | |
|---|---|---|
| WO | WO0121211 A1 | 3/2001 |
| WO | WO2007094779 A1 | 3/2007 |

OTHER PUBLICATIONS

J.R. Mazzeo et al., "A Phosphate Binding Assay for Sevelamer Hydrochloride by Ion Chromatography," J. Pharm. Biomed. Anal. (1999) 19, pp. 911-915.

"(logo) Renegal® Tablets (sevelamer hydrochloride) 400 and 800mg," Package insert (downloaded from http://www.fda.gov/cder/foi/label/2000/21179lbl.pdf).

* cited by examiner

PROCESS FOR THE PREPARATION OF SEVELAMER HYDROCHLORIDE AND FORMULATION THEREOF

RELATED APPLICATION

This application is a continuation of co-pending application Ser. No. 12/377,129, filed 11 Feb. 2009, which in turn claims priority from U.S. National Stage entry of PCT Application Serial No. PCT/IN2007/000387, filed 31 Aug. 2007, which in turn claims priority from India National application serial no. 1402/MUM/2006, filed 1 Sep. 2006, the contents of which are incorporated by reference here.

TECHNICAL FIELD OF THE INVENTION

The present invention relates to industrial process for preparation of Sevelamer hydrochloride. More specifically, the invention relates to improved process for crosslinking of polyallylamine hydrochloride dispersed in an organic medium with epichlorohydrin to obtain Sevelamer hydrochloride having phosphate binding capacity of 4.7 to 6.4 mmol/g.

The present invention further relates to pharmaceutical compositions of Sevelamer hydrochloride and a novel process for preparation of said compositions comprising high shear non-aqueous granulation.

BACKGROUND AND PRIOR ART

Sevelamer hydrochloride is poly(allylamine hydrochloride) crosslinked with epichlorohydrin in which 40% of the amines are protonated. Sevelamer is chemically known as poly(allylamine-co-N,N-diallyl-1,3-diamino-2-hydroxypropane) hydrochloride. Sevelamer hydrochloride is hydrophilic and swells, but is insoluble in water. The structure is represented below

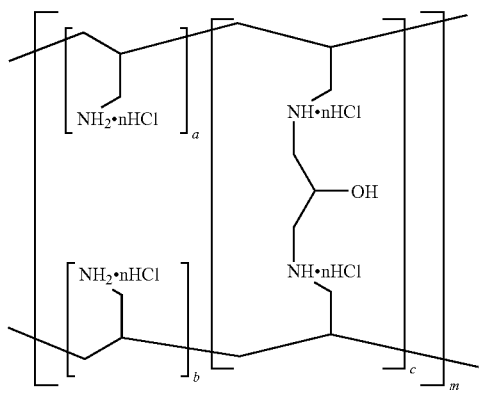

a, b = number of primary amine groups    a + b = 9
c = number of crosslinking groups    c = 1
n = fraction of protonated amines    n = 0.4
m = large number to indicate extended polymer network Sevelamer hydrochloride binds phosphate in the gastrointestinal tract to facilitate phosphorus excretion in feces, thereby inhibiting phosphorus absorption from the gut, and lowering the plasma phosphorus concentration. Patients with end-stage renal disease (ESRD) retain phosphate which lead to development of hyperphosphatemia. Phosphorus control is a primary goal in the care of patients with ESRD. Sevelamer hydrochloride which is a calcium-free, aluminium-free phosphate binder, allows physicians to control serum phosphorus in patients with ESRD who are on hemodialysis, without increasing serum calcium levels or contributing an excess calcium load. Clinical studies have shown that Sevelamer provides sustained reduction in markers of soft-tissue and cardiac calcification, such as serum calcium and phosphorus concentrations and parathyroid hormone and also improves blood lipid profiles. Thus, Sevelamer hydrochloride offers the promise of favourably impacting cardiac calcification and thereby reducing patient morbidity and mortality. Sevelamer hydrochloride taken with meals has been shown to decrease serum phosphorus concentrations in patients with ESRD who are on hemodialysis. Treatment of hyperphosphatemia includes reduction in dietary intake of phosphate, inhibition of intestinal phosphate absorption with phosphate binders and removal of phosphate with dialysis. Sevelamer hydrochloride treatment results in lowering of low-density lipoprotein (LDL) and total serum cholesterol levels. Sevelamer hydrochloride is indicated for the control of serum phosphorus in patients with Chronic Kidney Disease (CKD) on hemodialysis and contraindicated in patients with hypophosphatemia or bowel obstruction (see RENAGEL® sevelamer hydrochloride package insert, made of record in Applicant's Information Disclosure Statement). In hemodialysis patients, Sevelamer hydrochloride decreases the incidence of hypercalcemic episodes relative to patients on calcium treatment.

Sevelamer hydrochloride is marketed by Genzyme Corporation as RENAGEL® sevelamer hydrochloride 400 mg and RENAGEL® sevelamer hydrochloride 800 mg tablets. RENAGEL® sevelamer hydrochloride contains hypromellose, diacetylated monoglyceride, colloidal silicon dioxide, and stearic acid as inactive ingredients.

U.S. Pat. No. 5,496,545 discloses a method of removing phosphate from a patient by ion exchange, which involves oral administration of a therapeutically effective amount of a composition containing at least one phosphate-binding polymer that is non-toxic and stable once ingested. The polymers are orally administered, and are useful for the treatment of hyperphosphatemia. It also discloses spectrophotometric phosphate assay (PA) method to determine phosphate binding capacity (PBC) of crosslinked polyallylamine polymers. The PA value of Sevelamer hydrochloride obtained is 3.1 meq/g. It is also disclosed that it is desirous to have higher PA for better activity.

J. R. Mazzeo et al in J. Pharm. Biomed. Anal. 19 (1999) 911-915 teaches HPLC Ion Chromatography PA method for the determination of PBC (phosphate binding capacity) of Sevelamer hydrochloride. The average PA of three Sevelamer hydrochloride batches reported is 5.8 mmol/g.

Commercially available RENAGEL® sevelamer hydrochloride samples, when tested by the HPLC IC method was found to have PA about 5.3 mmol/g, chloride content of about 4.8 meq/g and degree of crosslinking in the range of 10% to 19%. The marketed product had remarkable consistency in its PBC but lacked consistency in its degree of cross linking.

U.S. Pat. No. 4,605,701 discloses process for preparing a cross-linked monoallylamine polymer. The method involves partially neutralizing polyallylamine hydrochloride followed by addition of epichlorohydrin and homogenization.

Further, the suspension obtained was dispersed into a liquid medium that is immiscible with the aqueous solvent in presence of Silvan S-83. However, the said patent does not deal with the properties and applications of the said polymer in phosphate binding.

WO 2006/097942 discloses biphasic process for crosslinking partly neutralized aqueous Polyallylamine hydrochloride using a crosslinking agent in a hydrocarbon solvent in presence of a dispersing agent to get a crosslinked polymer having a desired particle size range (60-100 mesh). The process is carried out in such a manner that aqueous solution is partly neutralized with alkali, mixed with crosslinking agent and charged to an organic phase containing dispersing agent. Crosslinking is carried out at a higher temperature and at a high speed of 800 to 1200 rpm. The crosslinked polymer is then isolated by filtration, followed by water washing to remove salts, followed by isopropyl alcohol (IPA) washing to remove water from the crosslinked polymer and finally drying in a stationary tray dryer.

U.S. Pat. No. 6,525,113 describes process for preparing crosslinked polyallylamine by mixing polyallylamine, water, a hydroxide or alkoxide and a water miscible organic solvent or co-solvent such as acetonitrile followed by the addition of crosslinking agent.

These processes disclosed in above prior arts have drawbacks which are as follows:

(a) Mixing of epichlorohydrin with aqueous solution of partially neutralised Polyallylamine hydrochloride is potentially a risky operation on a large scale because the crosslinking commences immediately upon mixing, which will eventually lead to gelling and pose problems in adding thus thickened gel to the organic phase on a large scale.

(b) The process is carried out at high speed of 800 to 1200 rpm.

(c) Recovery of water miscible solvents like acetonitrile is difficult thus making the process uneconomical and unsuitable on industrial scale.

(d) Washing with methanol or isopropylalcohol (IPA) generates excess of organic effluent, which increases the cost of goods and overheads.

(e) Methanol or IPA is extremely difficult to remove from the crosslinked polymer. Since Sevelamer hydrochloride is an Active Pharmaceutical Ingredient (API), it has to comply stringent ICH guidelines for Organic Volatile Impurities (OVI). Methanol being class II solvent as per the ICH guidelines is allowed maximum of 2000 ppm (0.2%) limit in API. IPA being class III solvent as per the ICH guidelines is allowed maximum of 5000 ppm (0.5%) limit in API. In the desired crosslinked polymer, IPA content is found much above 5000 ppm. The prescribed ICH limit is very stringent and difficult to achieve.

(f) Drying in stationary tray dryer imparts dark yellow colour to the polymer which remains unchanged even after swelling with water.

(g) The prior art processes are not amenable to large scale manufacture, cannot give the desired quality and are uneconomical. Thus there exists a need to develop an economically viable manufacturing process which is amenable to scale up and gives Sevelamer hydrochloride of superior quality.

Thus there is a need to develop a process for preparing Sevelamer hydrochloride with desired phosphate binding capacity, which simplifies the manufacturing method, minimizes the need for specialized equipments, brings down the need for wash solvents thereby bringing down the manufacturing costs. The present invention provides an economically viable process for preparation of Sevelamer hydrochloride suitable for industrial scale up.

EP0997148 by Chugai Pharmaceuticals discloses tablets which contains phosphate-binding polymers having an average particle size of 400 microns or less and 90% of particles are less than 500 microns and contains crystalline cellulose and/or hydroxypropylcellulose with low degree substitution. Tablets show a moisture content of 1 to 14%.

W00128527 discloses a tablet core which comprises at least about 95% by weight of an aliphatic amine polymer and a process of producing the tablet by hydrating the aliphatic amine polymer to the desired moisture level; blending the aliphatic amine polymer with the excipients in amounts such that the polymer comprises at least about 95% by weight of the resulting blend; and compressing the blend to form tablet core. Tablet is coated with a water based coating.

WO02085378 discloses a composition comprising a stable polyallylamine hydrochloride polymer wherein about 4% to about 12% by weight of the polymer is a chloride anion.

EP1153940 discloses phosphate binding polymer having a true specific gravity of 1.18-1.24 and process for producing phosphate binding polymer tablets.

Prior art discloses various formulations of Sevelamer by methods involving direct compression or dry granulation. However, the prior art further states that tableting of phosphate binding polymer Sevelamer by wet granulation is impossible and is difficult to achieve.

The inventors of the present invention tried out several ways for formulating Sevelamer hydrochloride and have successfully developed formulations by high shear non-aqueous granulation which provides improved cohesiveness of particles, excellent flowability and compression characteristics.

OBJECT OF THE INVENTION

The main object of the present invention is to provide industrial process for preparation of Sevelamer hydrochloride having PA in the range of about 4.7 mmol/g to about 6.4 mmol/g and chloride content in the range of about 3.74 to about 5.60 meq/g.

Another object of the invention is to provide pharmaceutical compositions comprising a therapeutically effective amount of Sevelamer hydrochloride along with suitable pharmaceutically acceptable excipients.

Another object of the invention is to provide a novel process for preparation of Sevelamer hydrochloride compositions comprising high shear non-aqueous granulation.

Another object of the invention is to provide improved and simplified process for preparation of Sevelamer hydrochloride which will eliminate the use of acetonitrile and the risk of gelling also avoid use of IPA for removing water.

Another object of the invention is to provide Sevelamer hydrochloride which will meet the stringent ICH (International Committee of Harmonisation) requirements.

Yet another object of the invention is to provide process which yields Sevelamer hydrochloride having consistency in degree of cross linking and avoids the need of specialized equipments for the manufacture of the said product and thereby reducing the manufacturing cost.

Still another object of the invention is to provide compositions for the control of serum phosphorus in patients with Chronic Kidney Disease (CKD) on hemodialysis.

Another object of the invention is to provide method for reducing the serum phosphorus in patients with Chronic Kidney Disease (CKD) on hemodialysis comprising administering a therapeutically effective amount of Sevelamer hydrochloride along with suitable pharmaceutically acceptable excipients.

SUMMARY OF THE INVENTION

The present invention discloses industrial process for preparation of Sevelamer hydrochloride having phosphate binding capacity of 4.7 to 6.4 mmol/g comprising the steps of (a) dissolving polyallylamine hydrochloride in water to obtain an aqueous solution;
(b) partially neutralizing the aqueous solution of polyallylamine hydrochloride with 65 to 70 mole % of alkali with respect to polyallylamine hydrochloride;
(c) charging dispersing agent to hydrocarbon solvent to obtain solution;
(d) mixing partially neutralized aqueous polyallylamine hydrochloride solution with the solution obtained in step (c);
(e) stirring the obtained reaction mixture at speed of about 40 to about 250 revolutions per minute to get fine dispersion of aqueous phase in organic phase;
(f) heating the suspension obtained in step (e) at an elevated temperature;
(g) charging 5 to 12% by weight of epichlorohydrin in relation to polyallylamine hydrochloride to the suspension of step (0 maintaining an elevated temperature till cross linking is complete;
(h) cooling the reaction mixture at temperature of 25 to 35° C. and isolating the compound by washing the obtained cake with water;
(i) drying the wet cake in a Fluidized Bed Dryer at temperature of about 25 to 90° C. to get Sevelamer hydrochloride with phosphate binding capacity of 4.7 to 6.4 mmol/gm.

In another aspect of the invention polyallylamine hydrochloride is prepared by reacting allylamine with hydrochloric acid to get allylamine hydrochloride salt and polymerising the obtained allylamine hydrochloride salt in presence of 2,2'-Azobis[2-methyl-N-(2-hydroxyethyl)propionamide (VA-086), a free radical initiator to get polyallylamine hydrochloride. The polyallylamine hydrochloride is having intrinsic viscosity of 0.14 to 0.22 decilitre/gm.

The present invention further discloses pharmaceutical compositions comprising a therapeutically effective amount of Sevelamer hydrochloride along with suitable pharmaceutically acceptable excipients. Said compositions are used in the control of serum phosphorus in patients suffering from chronic kidney disease (CKD) on hemodialysis. Further, the invention discloses a novel process for preparation of Sevelamer hydrochloride compositions comprising high shear non-aqueous granulation.

According to the present invention, the process for preparation of Sevelamer hydrochloride compositions comprising high shear non-aqueous granulation comprises the steps of:
(a) preparing a mixture of Sevelamer hydrochloride and one or more diluents;
(b) optionally wetting the mixture;
(c) preparing a non-aqueous binder solution by dissolving binder in an organic solvent;
(d) granulating the mixture of step (a) or step (b) using non-aqueous binder solution by high shear non-aqueous granulation to form granulated mass;
(e) drying the granulated mass;
(f) milling the dried mass using ball mill or fluid energy mill to form granules of suitable size;
(g) lubricating the milled granules;
(h) compressing the lubricated granules into tablets or filling the lubricated granules into capsules;
(i) coating the compressed tablets.

DETAILED DESCRIPTION OF THE INVENTION

Figure 1:
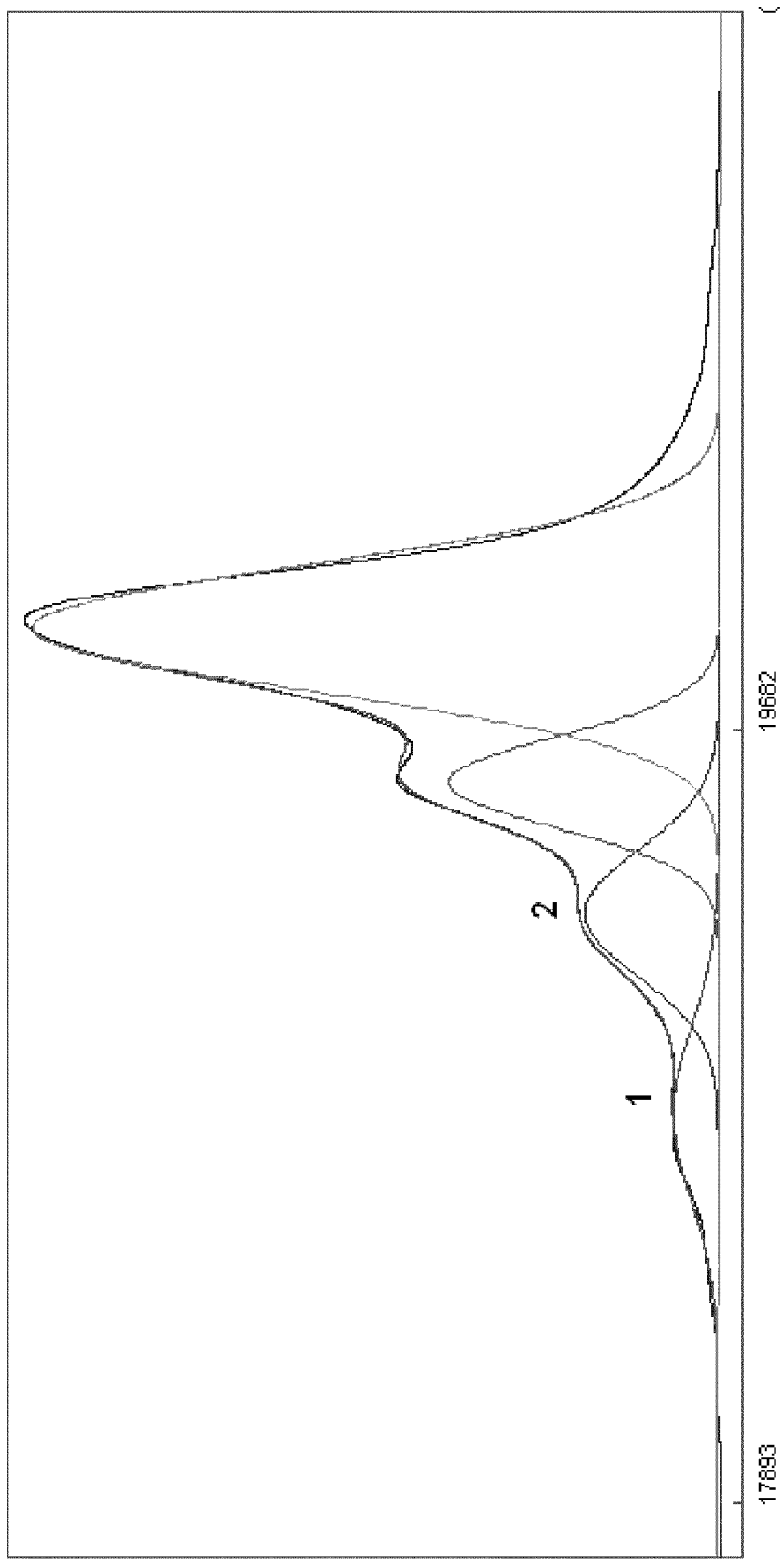
FIG. 1 shows powder $^{13}$C NMR of RENAGEL® sevelamer hydrochloride tablet

The present invention describes an industrial process for the preparation of Sevelamer hydrochloride. The present invention further involves improved process for crosslinking polyallylamine hydrochloride dispersed in an organic medium with epichlorohydrin to obtain Sevelamer hydrochloride having phosphate binding capacity of 4.7 to 6.4 mmol/g.

The present invention further describes pharmaceutical compositions comprising a therapeutically effective amount of Sevelamer hydrochloride along with suitable pharmaceutically acceptable excipients. A novel process for preparation of said Sevelamer hydrochloride compositions comprising high shear non-aqueous granulation is also described.

According to one embodiment of the invention process for preparation of Sevelamer hydrochloride according to the invention comprises the steps of;
(a) dissolving polyallylamine hydrochloride in water to obtain an aqueous solution;
(b) partially neutralizing the aqueous solution of polyallylamine hydrochloride with 65 to 70 mole % of alkali with respect to polyallylamine hydrochloride;
(c) charging dispersing agent to hydrocarbon solvent to obtain solution;
(d) mixing partially neutralized aqueous polyallylamine hydrochloride solution with the solution obtained in step (c);
(e) stirring the obtained reaction mixture at speed of about 40 to about 250 revolutions per minute to get fine dispersion of aqueous phase in organic phase;
(f) heating the suspension obtained in step (e) at an elevated temperature;

(g) charging 5 to 12% by weight of epichlorohydrin with respect to polyallylamine hydrochloride to the suspension of step (f) maintaining an elevated temperature till cross linking is complete;

(h) cooling the reaction mixture at temperature of 25 to 35° C. and isolating the compound by washing the obtained cake with water and filtration;

(i) drying the wet cake in a Fluidized Bed Dryer at temperature of about 25 to 90° C. to get Sevelamer hydrochloride with phosphate binding capacity of 4.7 to 6.4 mmol/gm.

In another embodiment of the invention polyallylamine hydrochloride is prepared by reacting allylamine with hydrochloric acid to get allylamine hydrochloride salt and polymerising the obtained allylamine hydrochloride salt in presence of (VA-086), a free radical initiator to get polyallylamine hydrochloride. The polyallylamine hydrochloride is having intrinsic viscosity of 0.14 to 0.22 decilitre/g.

According to the present invention polyallylamine hydrochloride is dissolved in water to obtain an aqueous solution of polyallylamine hydrochloride.

According to another embodiment of the present invention the aqueous solution polyallylamine hydrochloride is partially neutralized with alkali.

According to another embodiment of the invention alkali used is alkali metal hydroxide preferably sodium hydroxide.

In another embodiment of the present invention partial neutralization is carried out by adding 65 to 70 mole % of alkali with respect to polyallylamine hydrochloride, either as a solid or a solution. Moles of polyallylamine hydrochloride is calculated by dividing the weight of polyallylamine hydrochloride taken for reaction with molecular weight of allylamine hydrochloride. Using alkali in this range provides the chloride content in the desired range of about 4.3 to about 5.3 meq/g.

According to another embodiment of the present invention the dispersing agent is charged in hydrocarbon solvent.

According to yet another embodiment, the dispersing agent is selected from trioleate surfactants, preferably sorbitan trioleate (SPAN-85).

In another embodiment of the present invention, hydrocarbon solvent is selected from aliphatic or aromatic hydrocarbons preferably, aromatic hydrocarbons.

According to another embodiment of the present invention aromatic hydrocarbon is selected from benzene, toluene, xylenes, chlorobenzenes, nitrobenzenes or mixtures thereof.

In yet another embodiment of the present invention partially neutralized aqueous polyallylamine hydrochloride is mixed with hydrocarbon solvent containing dispersing agent in a conventional reactor and stirred at speed of about 40 to about 250 revolutions per minutes (RPM) to get fine dispersion of aqueous phase in organic phase followed by heating the suspension obtained at elevated temperature.

According to another embodiment of the present invention the speed for stirring the reaction mixture ranges from about 40 to about 250 revolutions per minute, preferably 40 to 60 revolutions per minute.

In another embodiment of the present invention elevated temperature ranges from about 40° C. to about 150° C., preferably 55 to 60° C.

In another embodiment of the present invention epichlorohydrin is charged at elevated temperature and maintaining the same temperature till cross linking is complete followed by cooling and isolating the cake of crosslinked polymer.

According to another embodiment of the present invention epichlorohydrin is used in the range of 5% to 12% by weight as compared to the weight of polyallylamine hydrochloride, preferably 6 to 9% by weight. Using epichlorohydrin in this range provides the PBC in the desired range of about 4.7 to 6.4 mmol/g. Using less than 5% quantity of epichlorohydrin results in a sticky. cross linked polymer and very poor yield due to water solubility, whereas using more than 12% quantity of epichlorohydrin lowers the PBC below 5.3 mmol/g.

In yet another embodiment of the invention, cooling is carried out by lowering the temperature to ambient temperature, preferably 25 to 35° C. and isolation is carried out by nutsching under suction or centrifuging, preferably centrifuging.

In another embodiment the obtained cake of crosslinked polymer is washed with water to remove sodium chloride salt and dried in Fluidized Bed Dryer (FBD) at temperature of about 25 to 90° C.; preferably at temperature range of 40° C. to 60° C. to get Sevelamer hydrochloride having phosphate binding capacity in the range 4.7 to 6.4 mmol/g.

The preparation of Sevelamer hydrochloride having phosphate binding capacity of 4.7 to 6.4 mmol/g is one of the important features of the present invention.

Elimination of IPA from the final isolation stage for removing water according to the present invention has a surprising effect on the physical property like appearance, swellability etc. of the cross linked polyallylamine. Another surprising effect of the process according to the present invention is that Sevelamer hydrochloride is obtained has higher PBC than that obtained by following an identical experiment carried out using IPA for water removal.

In a preferred embodiment of the invention, polyallylamine hydrochloride and water are mixed at 25 to 35° C. to get a clear solution. The solution is further cooled to 5 to 15° C. and aqueous solution of alkali (65-70 mole % by weight of polyallylamine hydrochloride) is added to the reaction mass at 5 to 15° C. and stirred for 30 minutes. Dispersing agent in hydrocarbon solvent is added to the obtained reaction mixture at 5 to 15° C. The temperature of the reaction mixture is then raised to 20 to 25° C. and maintained for 15 min. The reaction mixture is filtered to remove any extraneous matter at 25 to 35° C. and temperature of the obtained solution is further raised to 55 to 60° C. and maintained for 15 minutes. Epichlorohydrin (5-12% by weight of polyallylamine hydrochloride) is added to reaction mixture at constant temperature of 55 to 60° C. The reaction mixture is then cooled to 25 to 35'C and product is isolated by centrifugation. The wet cake is further sludged with water for 45 min. at 25 to 50° C. and filtered, then dried in FBD at 25 to 90° C.

Crosslinked polymer Sevelamer hydrochloride obtained by the process according to the invention is having chloride content from about 3.74 to about 5.6 meq/g, Phosphate Binding Capacity of about 4.7 to about 6.4 mmol/g and the degree of crosslinking from about 12% to about 18%.

Preferably, the chloride content ranges from about 4.3 to about 5.3 meq/g, Phosphate Binding Capacity of about 5.3 to about 6.0 mmol/gm and the degree of crosslinking from about 12% to about 16%.

Sevelamer hydrochloride as prepared by the present process and tested for PBC shows the following properties as below;

Karl Fischer<5% Loss on drying (LOD)<5%

The Sevelamer hydrochloride obtained by the present process is off-white in color and also swells more when suspended in water as compared to the Sevelamer hydrochloride obtained by following the process disclosed in WO 2006/097942. Capacity to swell more translates into higher PA by HPLC IC method which is shown in Table I below;

TABLE I

Sevelamer Hydrochloride Phosphate binding capacity by IC method:

| Sr. No. | Batch no. | Epichloro-hydrin % w/w | Sodium hydroxide % mole | Method | Phosphate binding capacity (mmol/g) |
|---|---|---|---|---|---|
| 01 | 122 | 9.0 | 69.0 | IPA wash-Tray drying | 5.26 |
| 02 | 123 | 9.0 | 69.0 | IPA wash-Tray drying | 5.17 |
| 03 | 130 | 9.0 | 69.0 | Water wash-FBD | 5.51 |
| 04 | 131 | 9.0 | 69.0 | Water wash-FBD | 5.48 |
| 05 | 128 | 11.8 | 69.0 | IPA wash-Tray drying | 4.95 |
| 06 | 121 | 11.8 | 69.0 | Water wash-FBD | 5.69 |

Figure 5:
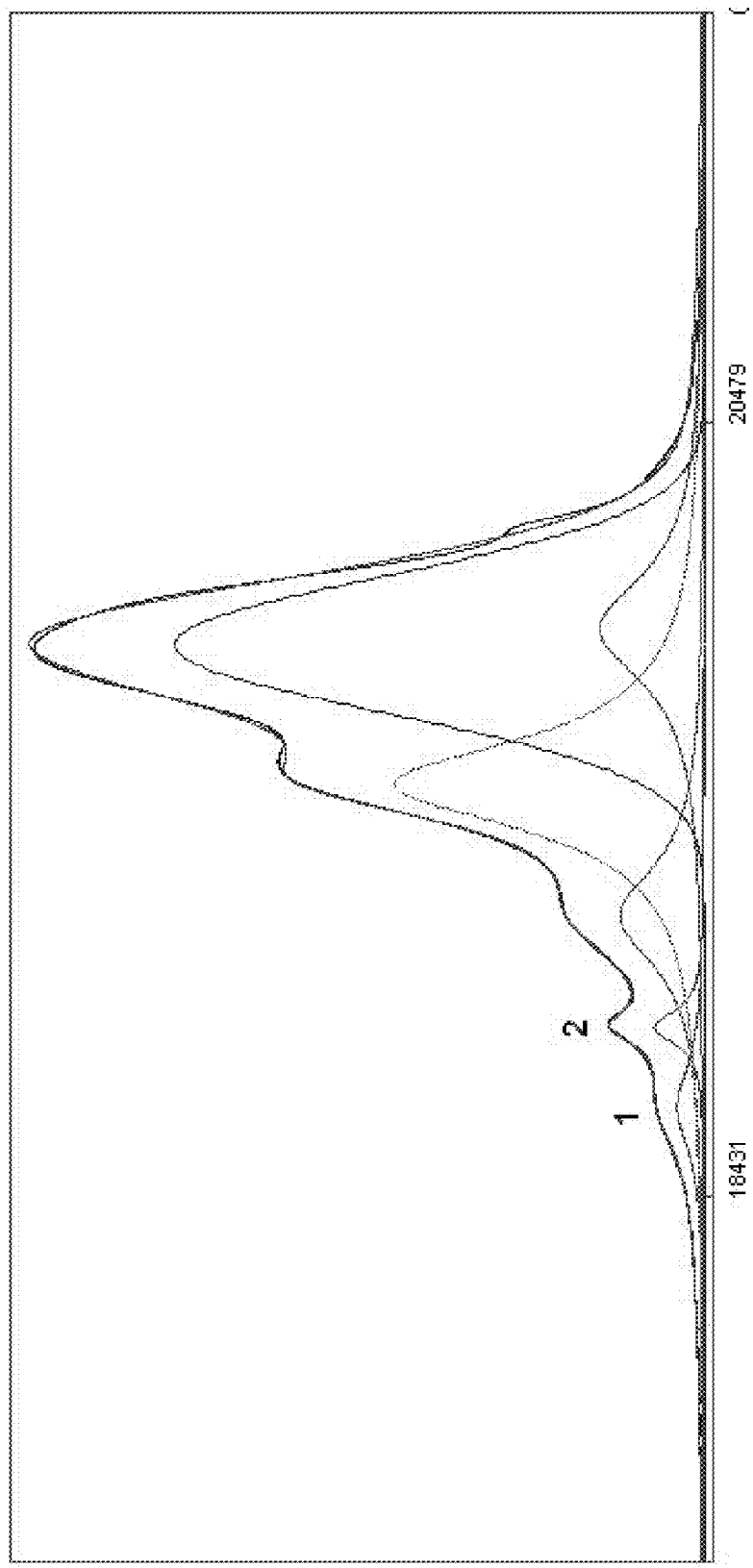
FIG. 5 shows powder $^{13}$C NMR of Sevelamer hydrochloride (API) obtained by following IPA wash-tray drying method.
Figure 6:
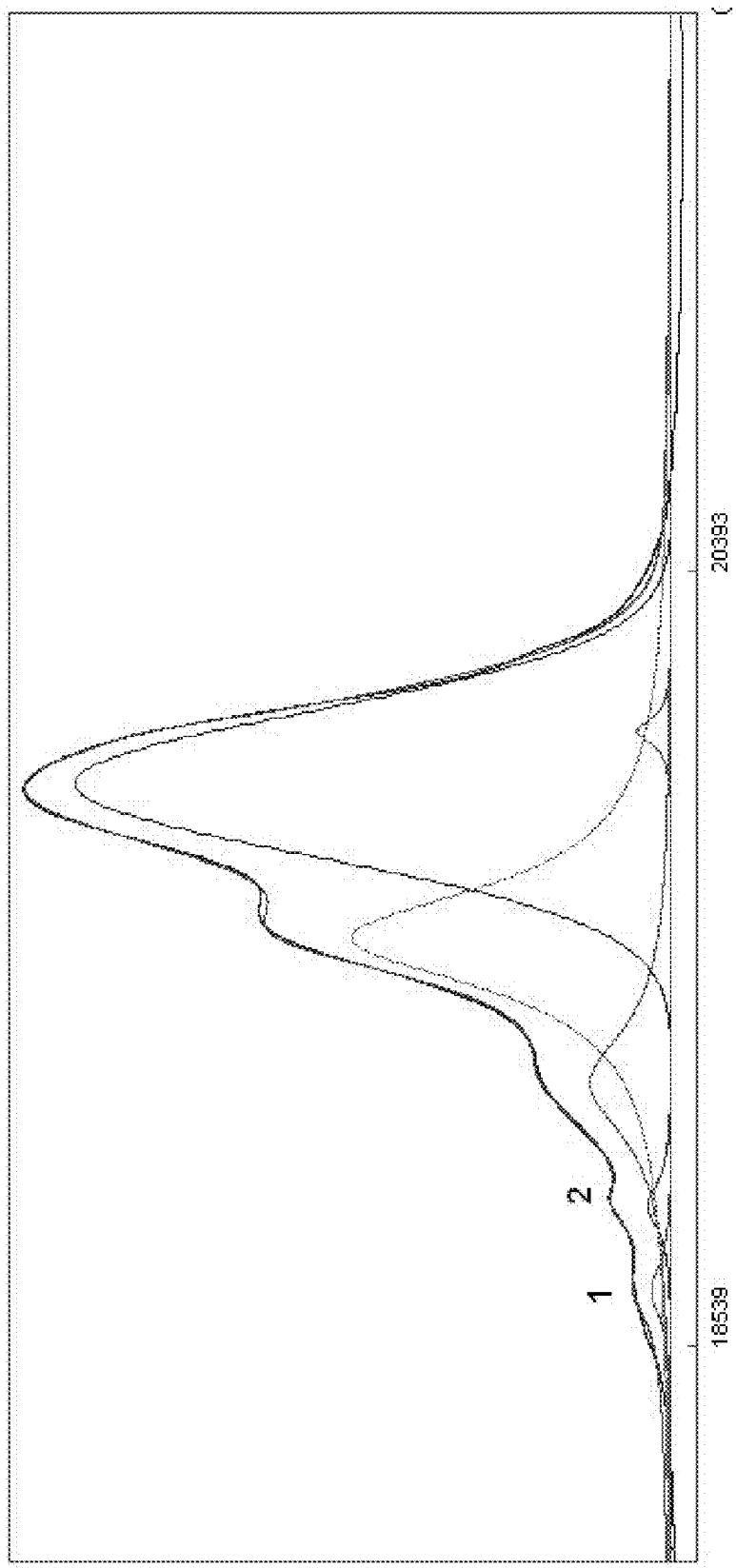
FIG. 6 shows powder $^{13}$C NMR of Sevelamer hydrochloride (API) obtained by following IPA wash-tray drying method.
Figure 7:
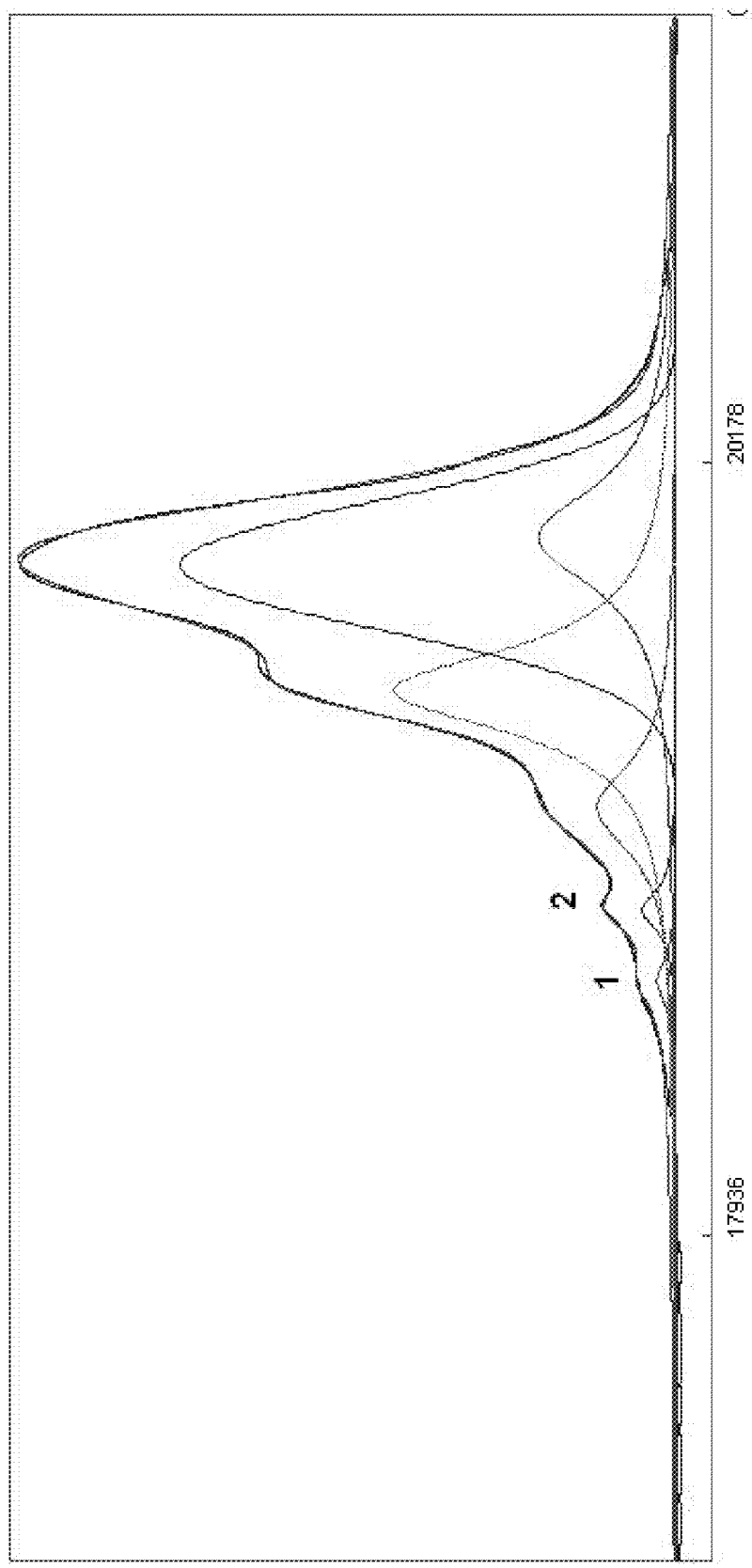
FIG. 7 shows powder $^{13}$C NMR of Sevelamer hydrochloride (API) obtained by following IPA wash-tray drying method.
Figure 8:
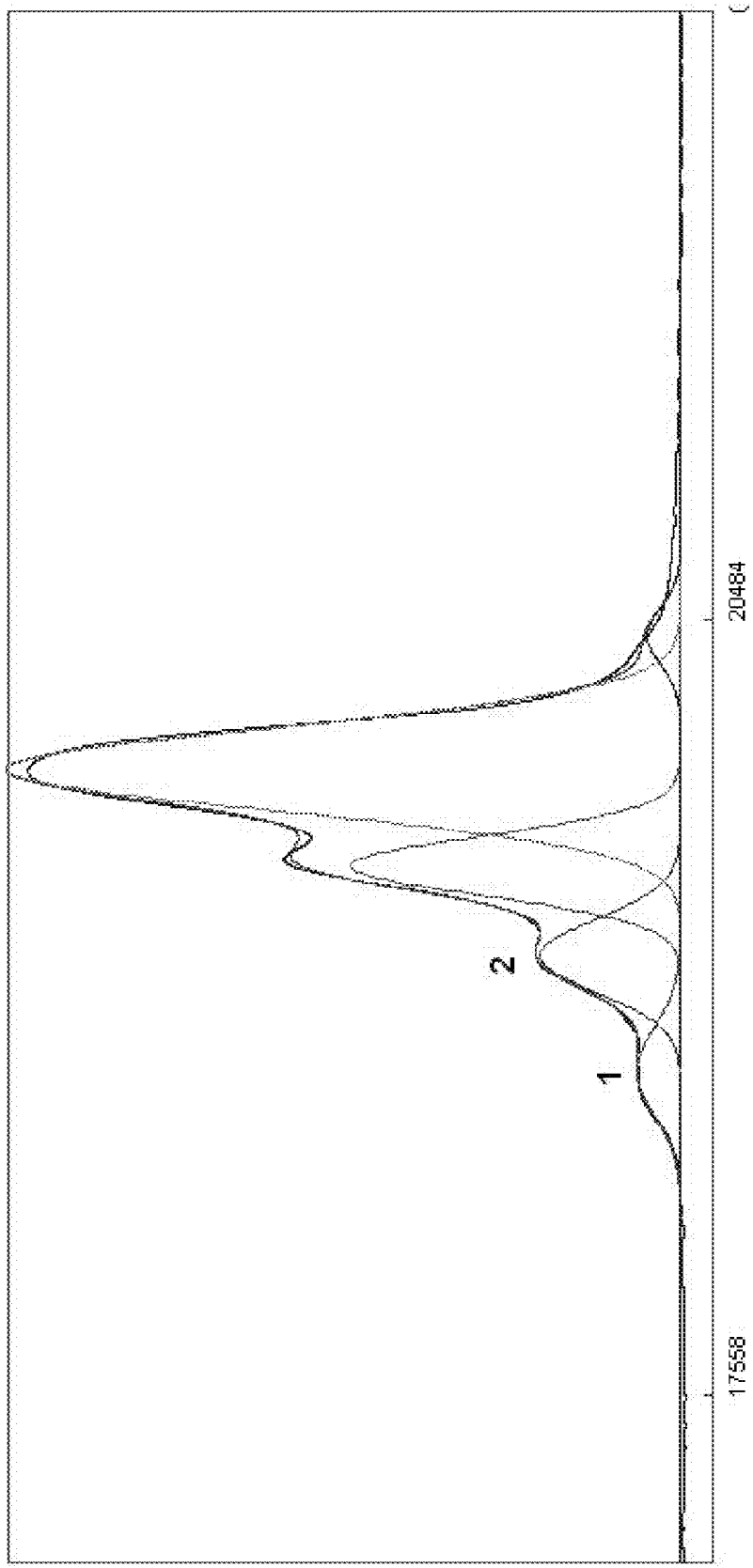
FIG. 8 shows powder $^{13}$C NMR of Sevelamer hydrochloride (API) obtained by following water wash—FBD method.
Figure 9:
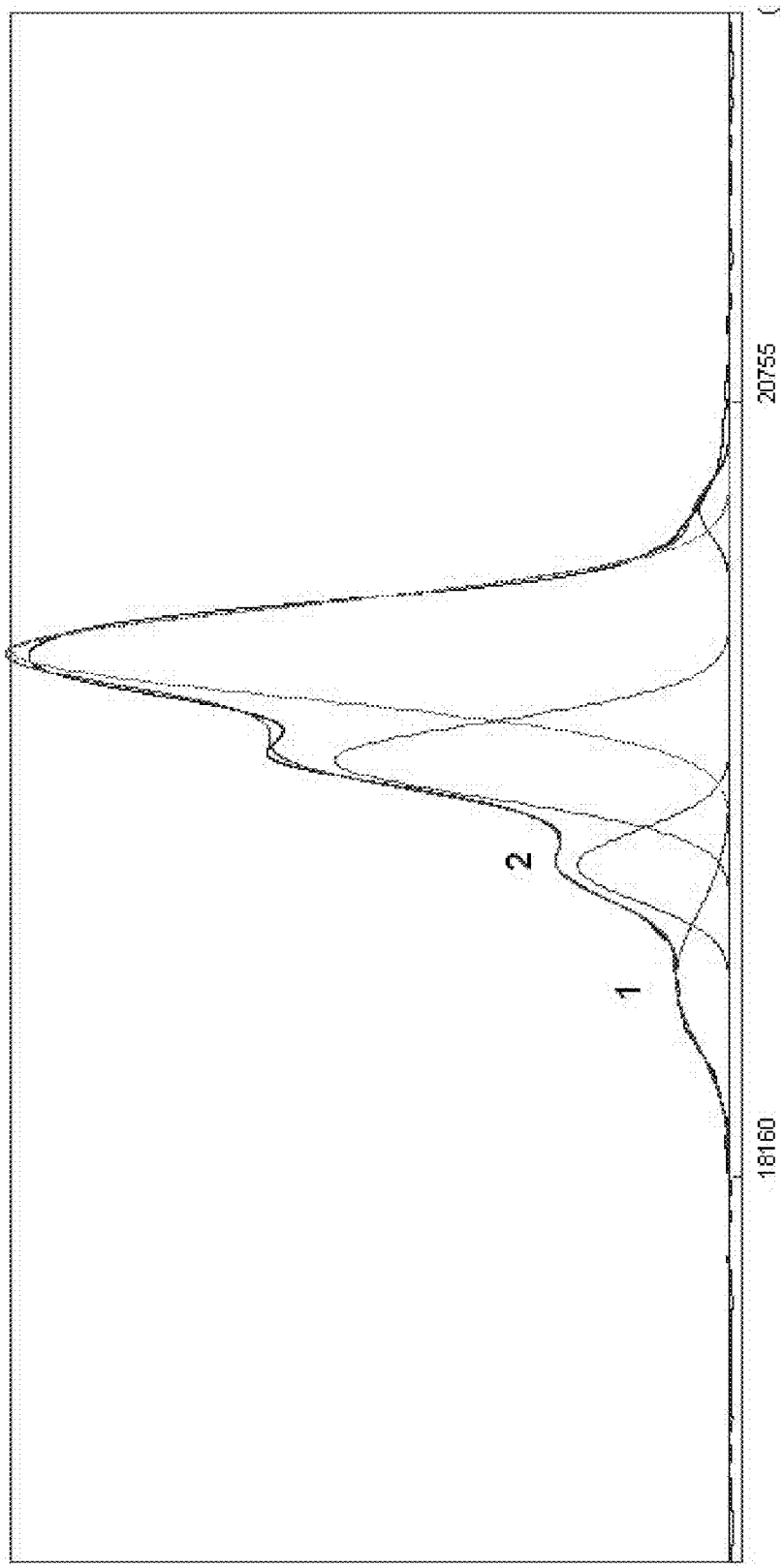
FIG. 9 shows powder $^{13}$C NMR of Sevelamer hydrochloride (API) obtained by following water wash—FBD method.
Figure 10:
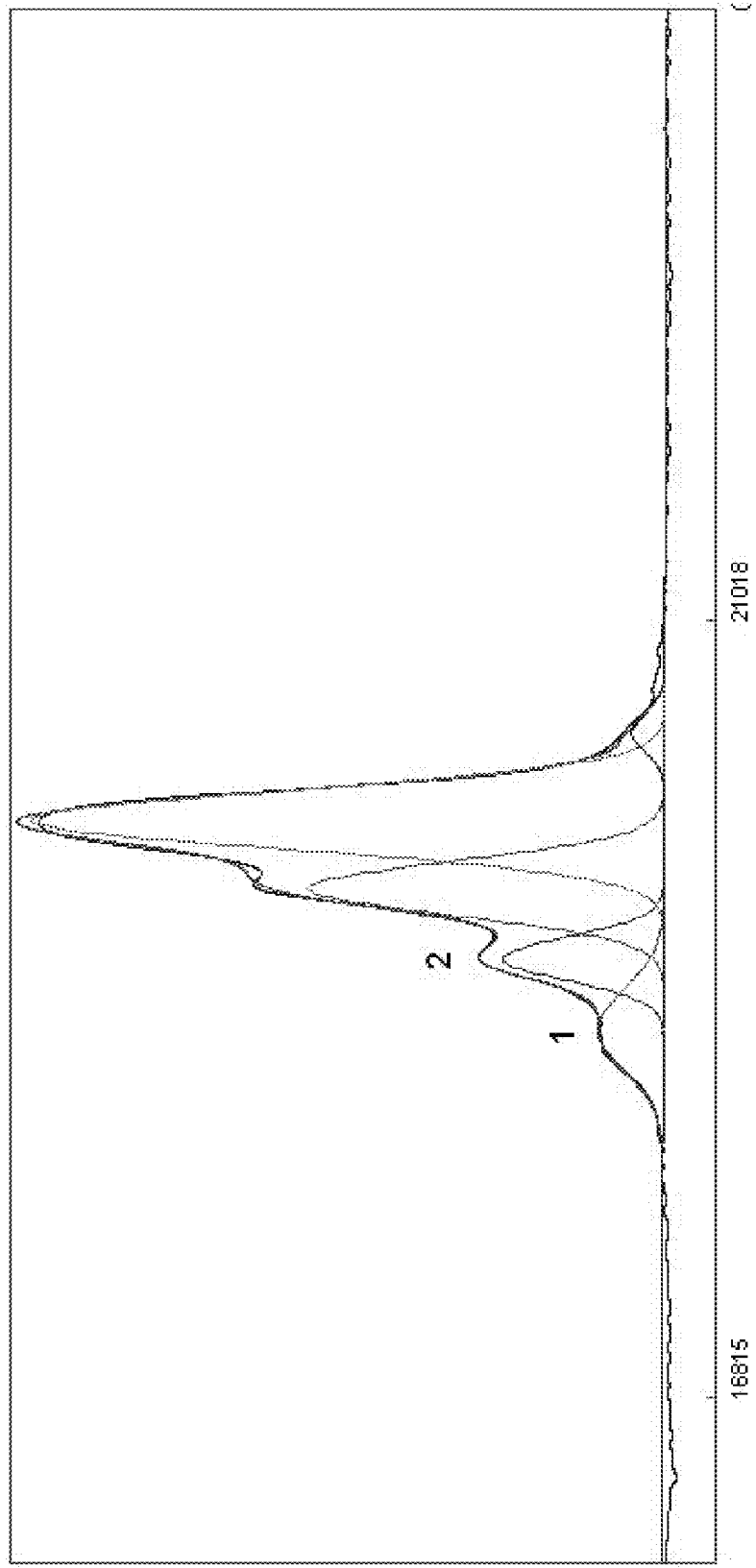
FIG. 10 shows powder $^{13}$C NMR of Sevelamer hydrochloride (API) obtained by following water wash—FBD method.

The process disclosed herewith also fulfills the objective of complying with ICH requirements. IPA contamination (peak 2) can be seen in the batches with IPA wash and dried in Tray drier [FIG. 5 (Batch no. 86), FIG. 6 (Batch no. 87) and FIG. 7 (Batch no. 89)], whereas no IPA contamination was observed in batches carried out with water wash and dried in FBD according to the present invention as shown in FIG. 8 (Batch no. 130), FIG. 9 (Batch no. 131) and FIG. 10 (Batch no. 121).

Figure 2:
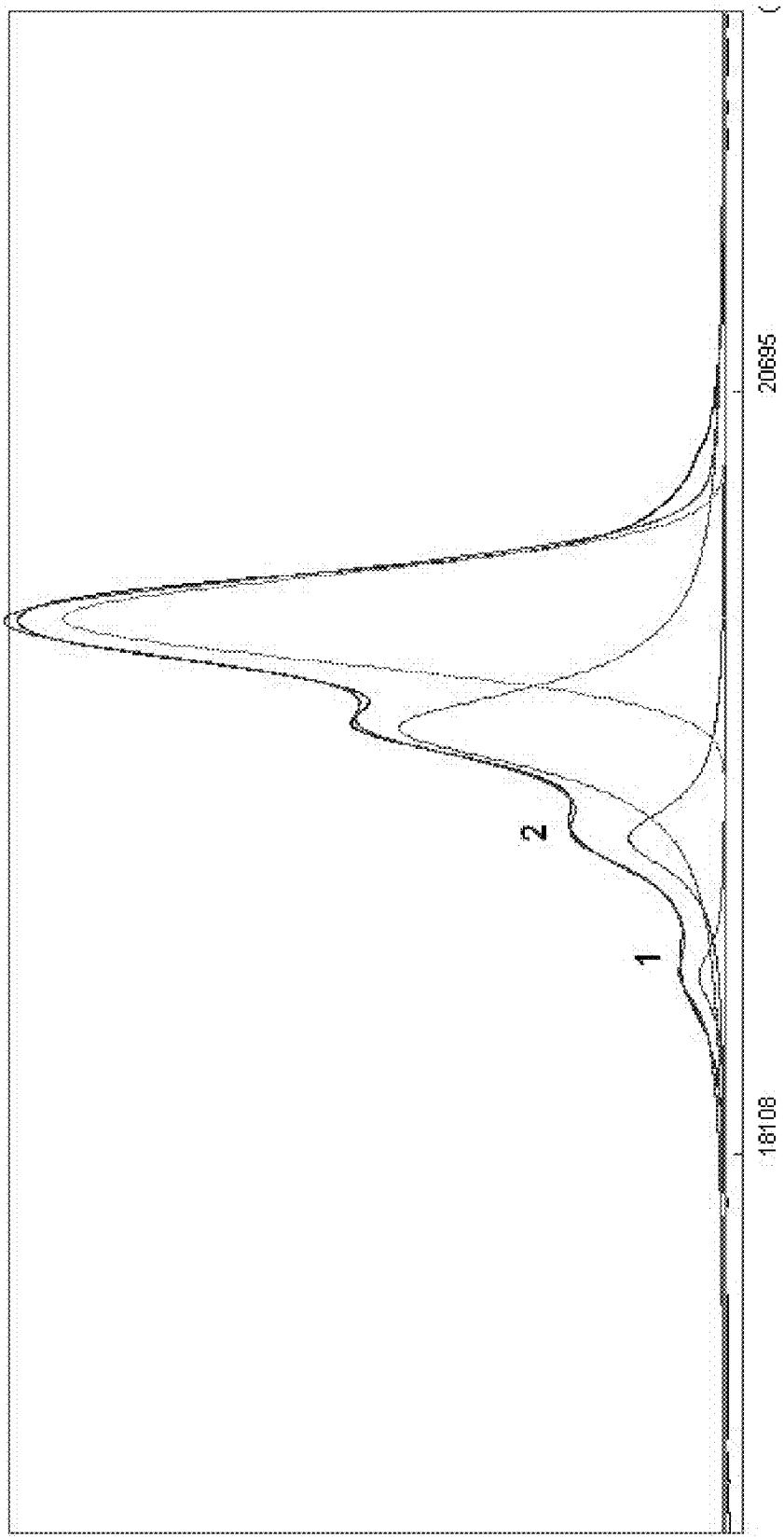
FIG. 2 shows powder $^{13}$C NMR of RENAGEL® sevelamer hydrochloride tablet
Figure 3:
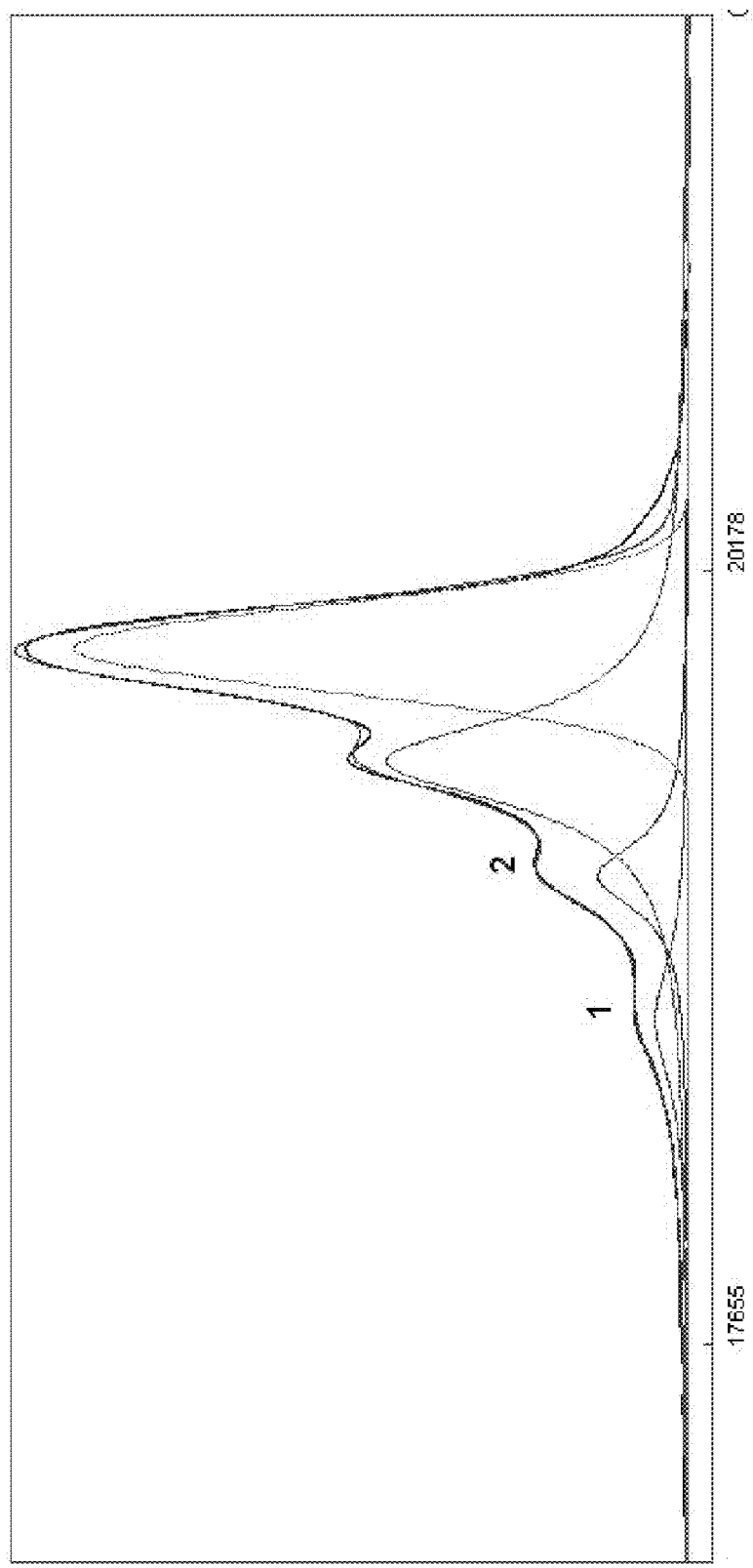
FIG. 3 shows powder $^{13}$C NMR of RENAGEL® sevelamer hydrochloride tablet
Figure 4:
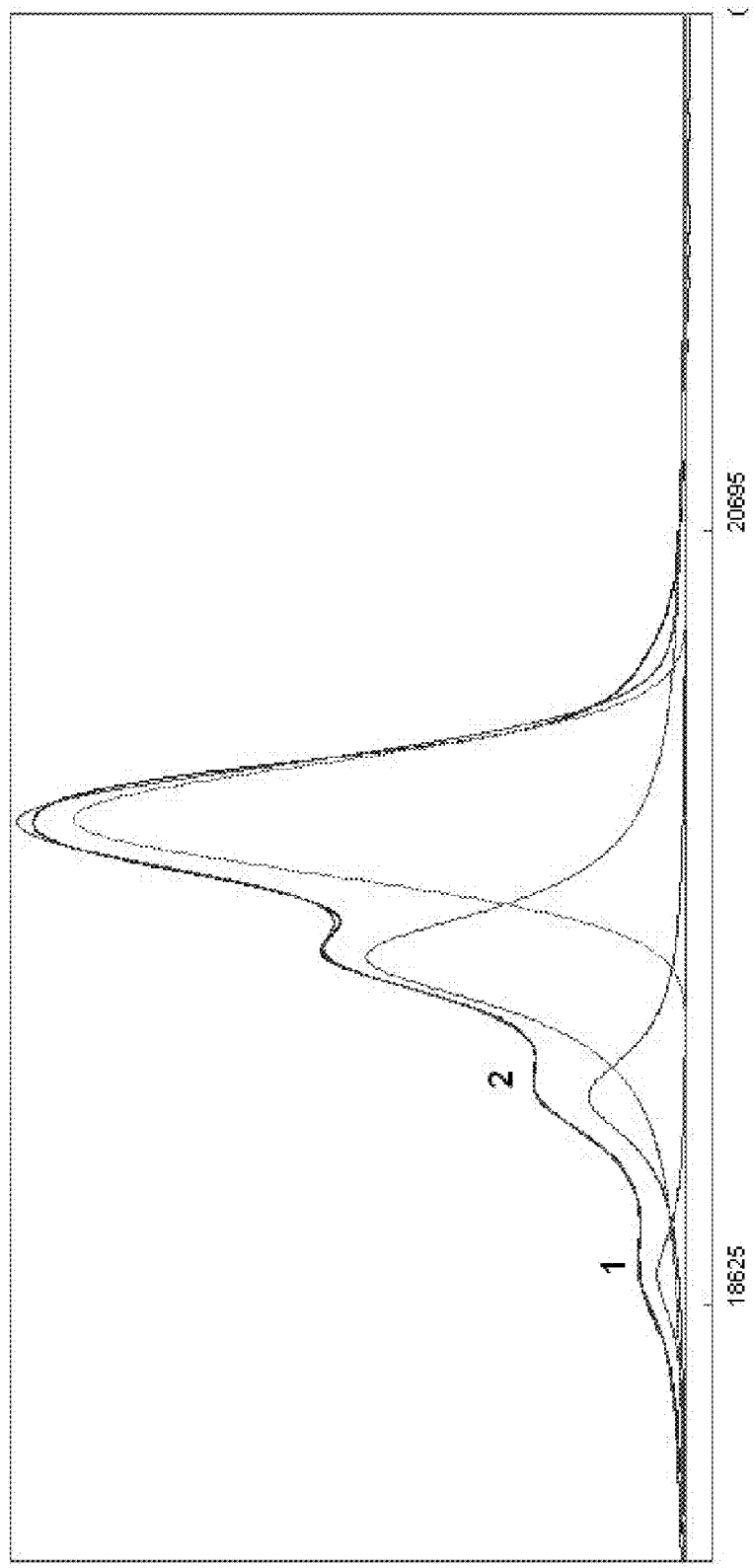
FIG. 4 shows powder $^{13}$C NMR of RENAGEL® sevelamer hydrochloride tablet

RENAGEL® sevelamer hydrochloride tablets were analyzed by solid state "C NMR technique. The area under the curve (AUC) of peaks 1 and 2 as shown in FIG. 1 (Batch no. 644871), FIG. 2 (Batch no. 45273 B), FIG. 3 (Batch no. 63455) and FIG. 4 (Batch no. 33685A) were determined by Powder "C NMR technique. The sum total of AUC of peak 1 and 2 is termed as the degree of cross linking in percentage.

The degree of crosslinking of RENAGEL® sevelamer hydrochloride formulation ranged from 10% to 19% (Table II). It was therefore desirable to produce Sevelamer hydrochloride having consistency in the degree of crosslinking. The object of the current invention is to produce the crosslinked polymer having degree of crosslinking in the range of 12% to 18%.

TABLE II

| Sr. No | Sample | Batch No. | % Epichlorohydrin | % Sodium Hydroxide | Chloride Content meq/g | PBC mmol/g | Degree of Crosslinking* |
|---|---|---|---|---|---|---|---|
| 1 | RENAGEL | 644871 | — | — | — | 5.32 | 18.19 |
| 2 | RENAGEL | 45273 B | — | — | 4.8 | 5.30 | 10.58 |
| 3 | RENAGEL | 33685 A | — | — | — | 5.30 | 12.29 |
| 4 | RENAGEL | 63455 | — | — | — | 5.28 | 13.87 |

*degree of crosslinkmg is based on the "C NMR recorded at National Chemical Laboratory, Pune.

Figure 11:
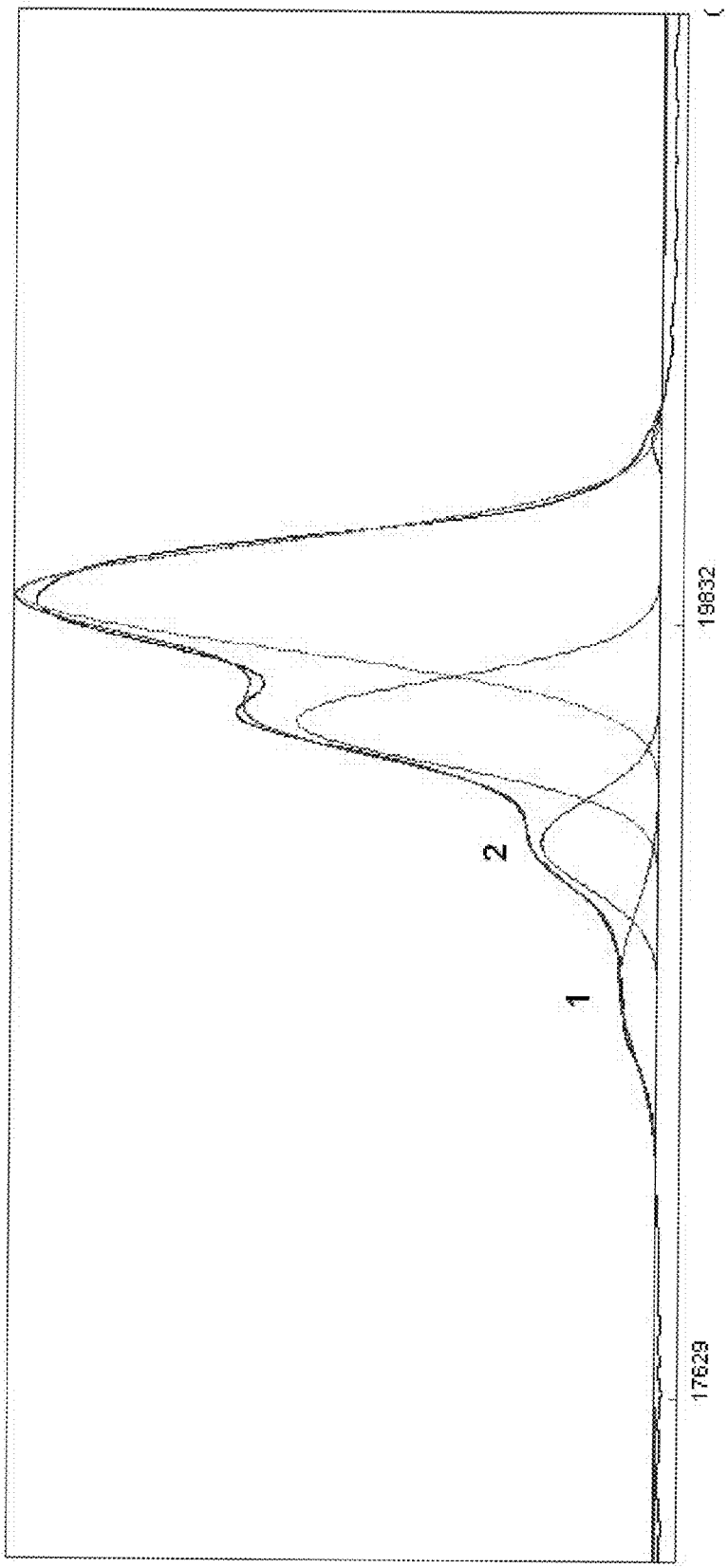
FIG. 11 shows powder $^{13}$C NMR of Sevelamer hydrochloride (API) obtained by the present process.
Figure 12:
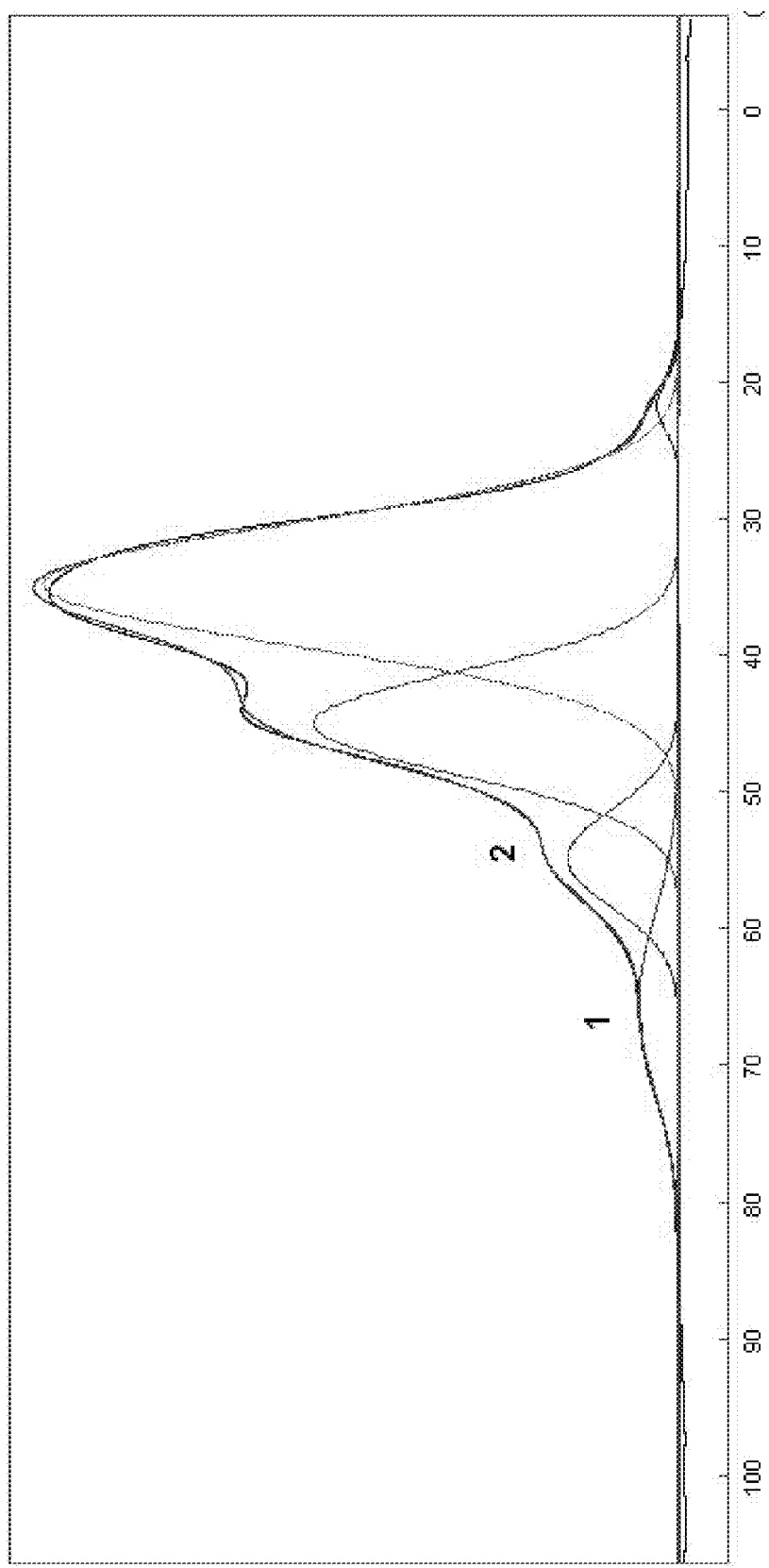
FIG. 12 shows powder $^{13}$C NMR of Sevelamer hydrochloride (API) obtained by the present process.
Figure 13:
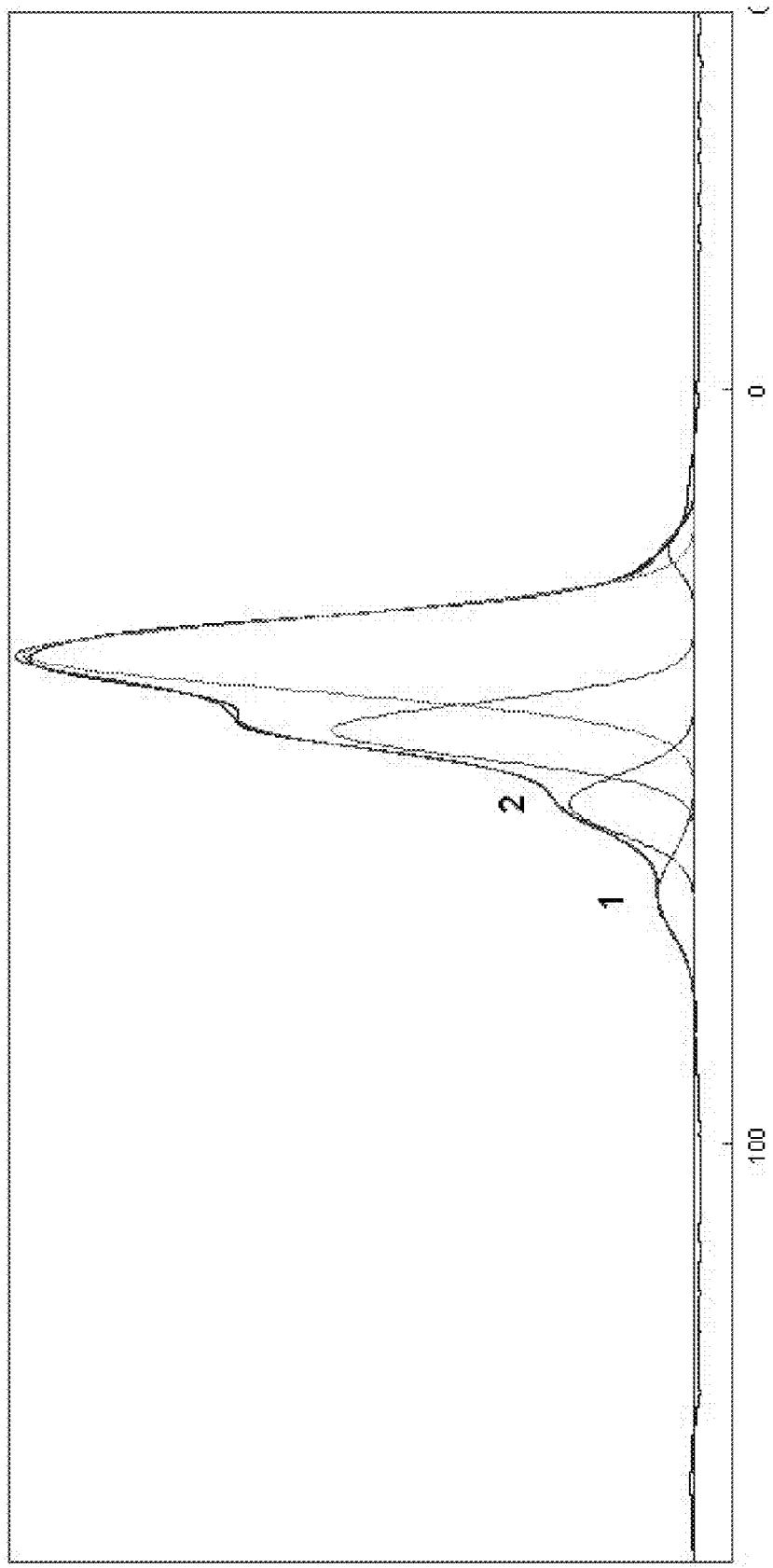
FIG. 13 shows powder $^{13}$C NMR of Sevelamer hydrochloride (API) obtained by the present process.
Figure 14:
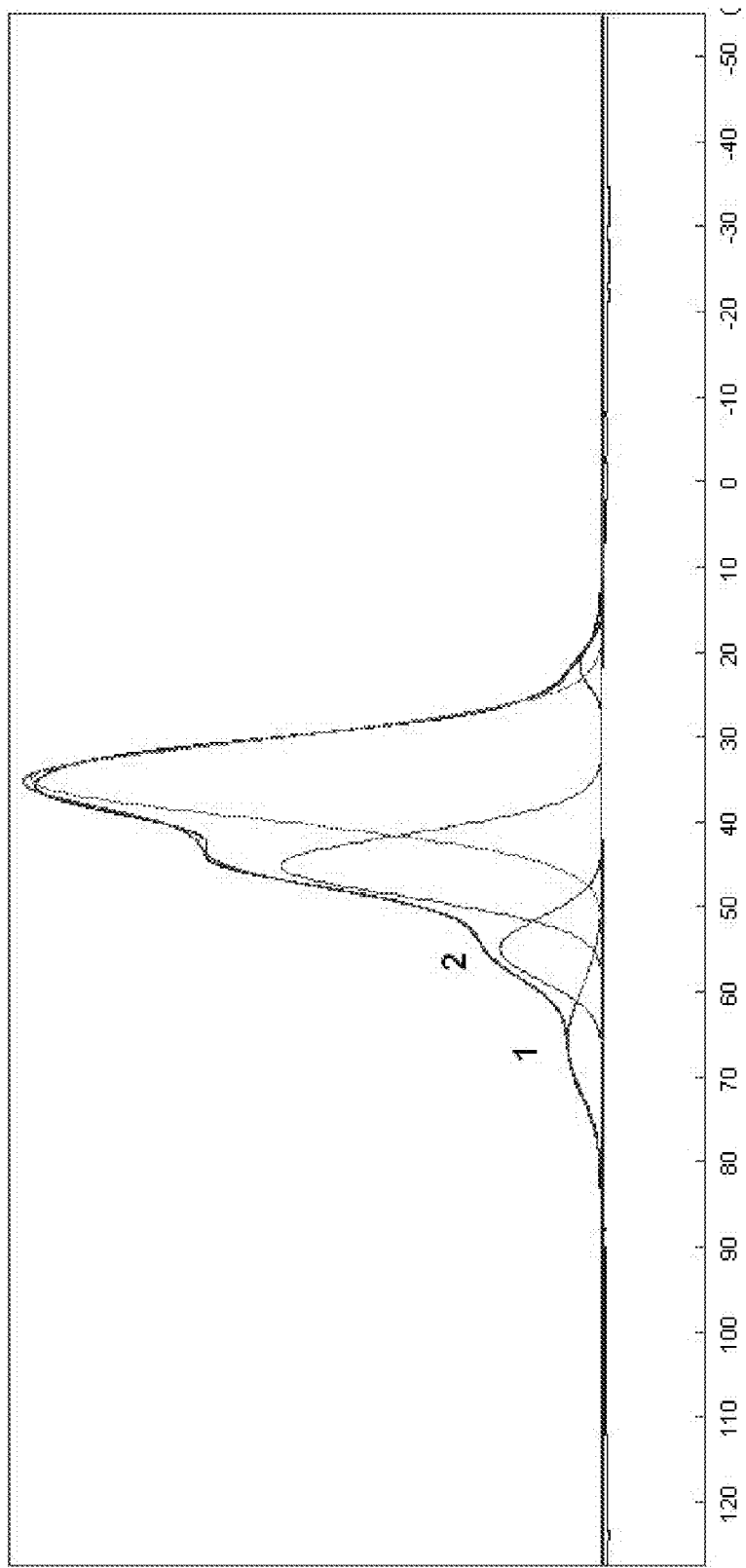
FIG. 14 shows powder $^{13}$C NMR of Sevelamer hydrochloride (API) obtained by the present process.

Thus the process disclosed herewith meets the primary objective of making Sevelamer hydrochloride having chloride content from about 3.74 to about 5.60 meq/g, Phosphate Binding Capacity of about 5.3 to about 6.0 mmol/g and consistent degree of crosslinking from about 12% to about 16% (Table III) as shown in FIG. 11 (Batch no. 99), FIG. 12 (Batch no. 132), FIG. 13 (Batch no. 133) and FIG. 14 (Batch no. 134).

TABLE III

| Sr. No. | Batch No. | % Epichloro-hydrin | % Sodium Hydroxide | Chloride Content meq/g | PBC mmol/g | Degree of crosslinking* |
|---|---|---|---|---|---|---|
| 1 | 99 | 6.79 | 65.5 | 4.80 | 5.39 | 13.80 |
| 2 | 132 | 6.79 | 65.5 | 4.79 | 5.44 | 13.21 |
| 3 | 133 | 6.79 | 65.5 | 4.64 | 5.54 | 13.14 |
| 4 | 134 | 6.79 | 65.5 | 4.60 | 5.42 | 13.12 |
| 5 | 130 | 9.00 | 69.0 | 4.68 | 5.51 | 15.38 |
| 6 | 131 | 9.00 | 69.0 | 4.47 | 5.48 | 15.39 |

*degree of crosslinking is based on the $^{13}$C NMR recorded at National Chemical Laboratory, Pune.

Sevelamer hydrochloride prepared by the process described by the present invention is used in formulating Sevelamer hydrochloride compositions.

Phosphate binding polymer Sevelamer is water insoluble but it swells in contact with water. Due to this tendency of swelling, formulating Sevelamer by aqueous granulation becomes difficult. Although attempts have been made to formulate Sevelamer by wet granulation method, none of the prior art discloses a successful process for high shear non-aqueous granulation being carried out in an equipment such as a high shear rapid mixer granulator or a planetary mixer.

Inventors of the present invention attempted granulation of Sevelamer hydrochloride using spray granulation technique. However, the results were not satisfactory since the binding solution containing ethylcellulose dissolved in isopropyl alcohol was very viscous and posed problem for uniform spraying of the granulating fluid on to the active ingredient and also the dry mass becomes tacky and forms sticky lumps.

Attempts were also made for preparation of Sevelamer hydrochloride compositions by hot melt granulation and hot melt extrusion techniques but the results were not satisfactory as very high quantity of binder was required and granules produced were lacking adequate flow properties.

Although the prior art states that tableting of a phosphate binding polymer such as Sevelamer hydrochloride is impossible by wet granulation, the inventors of the present invention have successfully developed a novel process for granulation of Sevelamer hydrochloride by high shear non-aqueous granulation.

According to the present invention, the process for preparation of Sevelamer hydrochloride compositions comprising high shear non-aqueous granulation comprises the steps of:

(a) preparing a mixture of Sevelamer hydrochloride and one or more diluents;

(b) optionally wetting the prepared mixture;

(c) preparing a non-aqueous binder solution by dissolving binder in an organic solvent;

(d) granulating the mixture of step (a) or step (b) with non-aqueous binder solution by high shear non-aqueous granulation to form granulated mass;

(e) drying the granulated mass;

(f) milling the dried mass using ball mill or fluid energy mill to form granules of suitable size;

(g) lubricating the milled granules;

(h) compressing the lubricated granules into tablets or filling the lubricated granules into capsules;

(i) coating the compressed tablets.

Figure 15:
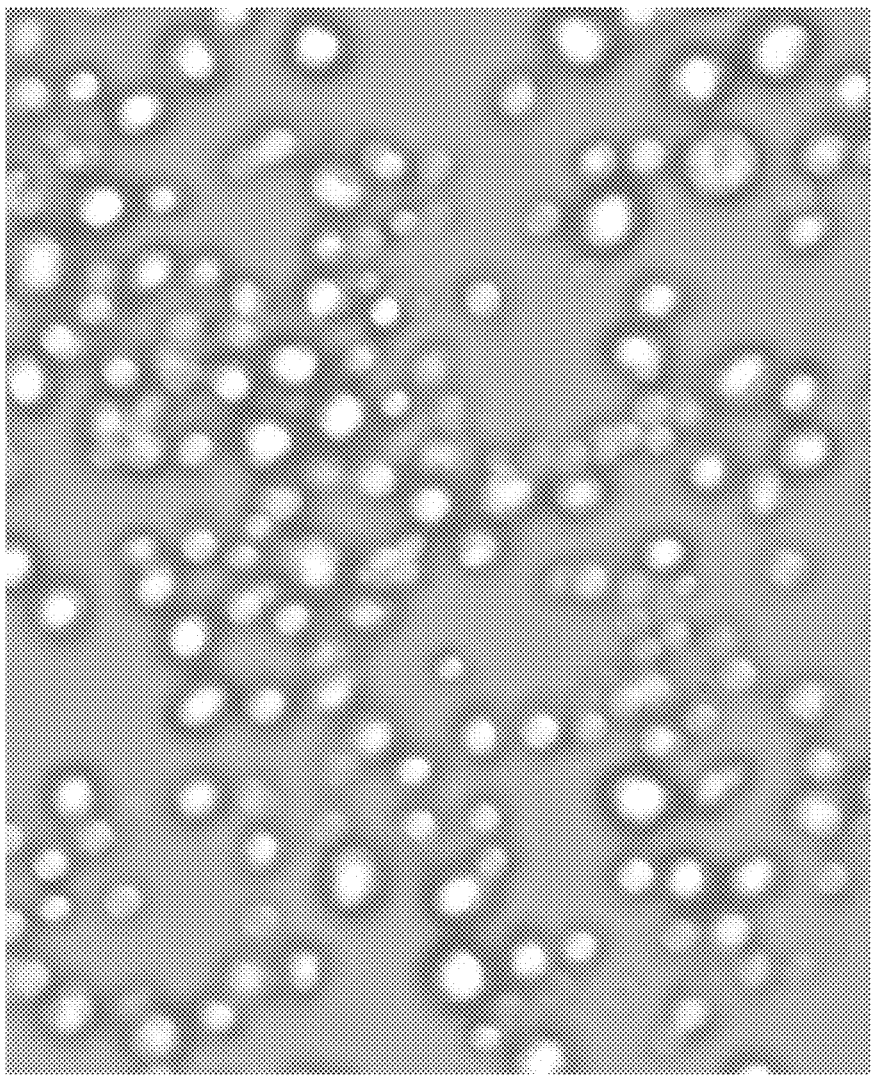
FIG. 15 shows shape of particles of Sevelamer hydrochloride (API) viewed through a microscope at a magnification of 40×.

According to the invention, the particles of Sevelamer hydrochloride are round in shape, particularly spherical or oval in shape (ref. FIG. 15). Spherical or oval shaped particles of Sevelamer hydrochloride have low bulk density and poor flowability and further resist size reduction. Particles resist deformation and do not rupture or fracture. Due to these characteristics of Sevelamer hydrochloride, formulating Sevelamer hydrochloride by direct compression method becomes extremely difficult. In the practice of the present invention, although the spherical morphology and hydrophilic nature of active ingredient Sevelamer hydrochloride presents a special challenge to the formulator, the inventors of the present invention have successfully prepared Sevelamer hydrochloride compositions by high shear non-aqueous granulation and by using rapid mixer granulator or planetary mixer.

According to one embodiment of the invention, the process of preparation of Sevelamer hydrochloride by high shear non-aqueous granulation comprises providing a mixture of active ingredient Sevelamer hydrochloride and one or more diluents; wetting the said mixture using purified water; further granulating by non-aqueous granulation using a non-aqueous solvent and preferably by using a non-aqueous binder solution prepared by dissolving the binder in an organic solvent; the granulation process being carried out in a rapid mixer granulator. Granulated mass is dried. Dried mass is further milled or pulverized to get granules size less than 425 microns (40#) and preferably less than 250 microns (60#) using a multi-mill initially and then a fluid energy mill or a ball mill and preferably using a ball mill. Milled or pulverized granules are lubricated using lubricants known in the art and further compressed to provide tablets of required size. Compressed tablets are further film coated by non-aqueous coating or aqueous coating or by hydroalcoholic coating.

According to a preferred embodiment, the process of preparation of Sevelamer hydrochloride compositions comprises mixing Sevelamer hydrochloride with one or more diluents; wetting the mixture using a solution of polyethylene glycol 6000 (Macrogol) dissolved in purified water; preparing a non-aqueous binder solution by dissolving polyvinyl pyrrolidone (Povidone K-30) in an organic solvent such as isopropyl alcohol; further granulating using the said non-aqueous binder solution and drying the granules. Sizing the dried granules through 60# on vibrosifter after milling with multi-mill and ball mill and further blending with commonly used lubricants and compressing the granules. Core tablets are further film coated by aqueous process till a weight gain of 4.0% to 6.0% is achieved.

Sevelamer hydrochloride is not a free flowing powder and is bulky. Wetting with purified water helps in decreasing the interparticulate distance and increasing the contact area between the particles; thus making Sevelamer Hydrochloride more amenable for the non-aqueous granulation. Wetting is carried out either in a rapid mixer granulator or a planetary mixer. In the practice of the present invention, wetting of mixture of active and diluent is carried out using about 2% to 9% by weight of purified water. Alternatively, the mixture of active and diluent may be made wet using a solution of polyethylene glycol dissolved in purified water. In an alternate method, polyethylene glycol 6000 may be added into the dry mix as a fine powder during the mixing step. Polyethylene glycols of various grades may be used such as polyethylene glycol 6000 or the like.

In the practice of the present invention, non-aqueous granulation is carried out by adding the binder slowly in a thin stream continuously using a peristaltic pump under high speed mixing with the impeller 'on' and chopper 'off'. On completion of binder addition, mixing is continued at high impeller speed till cohesive granular mass is obtained. If the mass is lumpy then chopper may be used at high speed with impeller also at high speed to obtain uniform wet mass.

High shear non-aqueous granulation as practiced by the present invention improves the cohesiveness of particles and provides excellent flowability and compression characteristics to the tablet. As the granules exhibit good flow properties, tablets produced possess uniformity in weight.

Drying of granulated mass may be carried out using fluidized bed drier or tray drier. Initial drying is performed without application of temperature and further the granulated mass is dried for sufficient time at about 45° C. to 50° C. till loss on drying value is achieved in the range of about 8.0% to about 10.0% when about 9.0% water is used or a lower loss on drying value considering the amount of water used for wetting. If planetary mixer is used for granulation, the wet mass is to be milled on a multi-mill using 8.0 mm screen and then charged for drying.

According to a preferred embodiment, the process comprises mixing Sevelamer hydrochloride with one or more diluents; optionally wetting the mixture using purified water in a rapid mixer granulator; preparing a non-aqueous binder solution by dissolving ethyl cellulose in an organic solvent such as isopropyl alcohol; granulating the mixture of Sevelamer hydrochloride and diluents using the said non-aqueous binder solution and drying the granules. Sizing the dried granules through 60# on vibrosifter after milling initially with multi-mill and further with ball mill and further blending with commonly used lubricants and compressing the granules. Core tablets are further film coated.

According to a more preferred embodiment, Sevelamer hydrochloride is mixed with mannitol and made wet using purified water; granulated using non-aqueous binder solution prepared by dissolving ethyl cellulose in isopropyl alcohol. Granulation is carried out in a rapid mixer granulator and the granulated mass is dried till loss on drying of about 9.0% is achieved. Dried mass is sized using ball mill to achieve granules of required size; lubricated using lubricants and compressed into tablets or filled into capsules.

According to another embodiment of the invention, the process of preparation of Sevelamer hydrochloride composition comprises providing a mixture of active ingredient Sevelamer hydrochloride and one or more excipients; granulating the mixture by high shear non-aqueous granulation using a non-aqueous solvent and preferably by using a non-aqueous binder solution prepared by dissolving the binder in the non-aqueous solvent; the granulation process being carried out in a rapid mixer granulator. Granulated mass is further dried and a loss on drying value in the range of about 3.0% to 5.0% (which is similar to loss on drying of active Sevelamer hydrochloride) is achieved. Dried granules are further milled or pulverized to get granules size of 425 microns (40#) and preferably less than 250 microns (60#) using a fluid energy mill or a ball mill and preferably by using a ball mill. Milled or pulverized granules are lubricated using lubricants known in the art and further compressed to provide tablets of required size or filled into capsules. Compressed tablets may be further coated.

According to one embodiment, the granules provided by high shear non-aqueous granulation process as described herein are spherical granules of size less than 425 microns, preferably less than 250 microns. Although the dried mass can be milled or pulverized using conventional equipments known in the art such as a multimill, co-mill, cadmill or fitzmill, they have limitations when used for size reduction of Sevelamer hydrochloride granules. Granule size below 425 microns (which passes through 40#) is difficult to obtain using conventional mills. Large granules pose difficulties during compression by decreasing the compressibility of the granules and produces porous tablets with low hardness which consequently exhibit high friability and pose a risk of moisture uptake during aqueous film coating. Oversized granules retained after milling through 0.5 mm screen on a conventional mill and sifting on a vibrosifter through 60# are milled in a ball mill or fluidized energy mill to obtain a granule size below 425 microns, preferably below 250 microns.

According to the invention, size reduction or pulverization using fluid energy mill or ball mill provides spherical granules of size less than 250 microns, which provides an ease in compressibility. Ball milling being the preferred mode for size reduction of granules. In ball milling, the process of size reduction occurs due to combined effect of impact and attrition. In a Fluid energy mill, the material is suspended and conveyed at high velocity by air, which is passed through nozzles at 100 to 150 pounds per square inch. The violent turbulence of the air reduces the particle size by interparticulate attrition. Ball mill is preferred in terms of output and productivity for large scale batches.

Milled mass is further sifted through a vibrosifter and oversized granules are milled through a mill preferably a ball mill with stainless steel balls and further sifted through a vibrosifter. Mass is milled with ball mill and sifted through vibrosifter till the resultant granules passed through 60#. According to a preferred aspect, granules of the present invention preferably have a granule size of 100% passing through 60# or 40#. Granule size of 250 microns or less provide satisfactory compression of granules and further provides elegant non-porous, non-friable tablets with a smooth impervious surface which can withstand the rigours of aqueous film coating.

In the practice of the present invention, the granule size is controlled such that 100% granules passes through 60# and provides tablets which exhibit a smooth impervious surface with a hardness greater than 100 N, friability less than 0.8%, preferably in the range of 0 to 0.1% and disintegration time of about 5 minutes, and a smooth aqueous film coating operation. By controlling the granule size at less than 425 microns (which passes through 40#) and preferably less than 250 microns (which passes through 60#), elegant tablets are produced.

In a preferred embodiment, coating of tablets is done using an aqueous coating method. Aqueous coating of an hydrophilic active ingredient is another difficult process and posed a real challenge to the inventors of the present invention as the Sevelamer hydrochloride has a tendency to swell in presence of water. Aqueous coating has been achieved by having a fine control on the hardness of the cores, which balances the need for a hard core to ensure good coating as well as meets the requirement for disintegration of coated tablets. As the tablet core is hard with an impervious smooth surface, it withstands the aqueous film coating and the polymer Sevelamer hydrochloride does not swell during coating.

Film coating may be carried out using polymers such as polyvinyl alcohol, hydroxyethyl cellulose, ethylcellulose, hydroxypropyl methyl cellulose, methacrylicacid co-polymers. Ready mix coating materials may comprise plasticizers selected from propylene glycol, triacetin or polyethylene glycol. Coating agents may be used in the range of about 3.0% to about 8.0% by weight of total composition.

Tablets may be compressed using suitable punches and dies. Tablets may be of oval, elliptical, spherical or caplet shape. Compression can be carried out using equipments known in the art such as a rotary tablet press. Tablets prepared by the process according to the invention meet the specification for disintegration (Limit not more than 30 minutes). Other parameters of tablets such as hardness, friability, and thickness, were measured and the results met the prerequisites of established acceptance criteria.

Compositions of Sevelamer Hydrochloride, particularly the tablets may be packed in aluminium strips or by cold formed blister pack, which is a cold process of blister packing, which acts as an excellent moisture barrier with negligible moisture vapor transmission rate and adequate environmental protection during shelf life. Tablet or capsule compositions may also be bulk packed optionally with a dessicant.

According to another embodiment, the spherical granules produced by the high shear non-aqueous granulation process may be filled along with suitable excipients into hard gelatin capsules of suitable size. Capsule filling can be done using a suitable capsule filling machine.

The present invention further provides pharmaceutical compositions comprising a therapeutically effective amount of Sevelamer hydrochloride along with suitable pharmaceutically acceptable excipients. Said compositions are used in the control of serum phosphorus in patients suffering from chronic kidney disease (CKD) on hemodialysis.

According to one embodiment, the compositions of the present invention comprises the active ingredient Sevelamer hydrochloride in the range of about 66.0% to about 80.0% by weight of total composition. More particularly, Sevelamer hydrochloride compositions of the present invention may be provided in dose strength of 400 mg and 800 mg which are scaleup/scaledown formulations.

According, to a preferred embodiment, the compositions contain about 66.0% to about 80.0% by weight of Sevelamer hydrochloride, about 5.0% to about 21.0% by weight of diluent, about 3.0% to about 15.0% by weight of binder, about 0.10% to about 3.0% by weight of glidant, about 0.10% to about 3.0% by weight of lubricants and about 3.0% to about 8.0% by weight of coating agents.

According to another preferred embodiment, the compositions contain 70.0% to 72.0% by weight of Sevelamer hydrochloride, 7.0% to 10.0% by weight of mannitol, 7.35% to 7.5% by weight of ethyl cellulose, 0.25% to 0.3% by weight of colloidal silicon dioxide, 0.25% to 0.3% by weight of lubricants and 5.0% to 6.0% by weight of coating agents.

According to yet another preferred embodiment, the compositions contain 75.0% to 78.0% by weight of Sevelamer hydrochloride, 7.0% to 10.0% by weight of mannitol, 7.35% to 8.0% by weight of ethyl cellulose, 0.6% to 0.9% by weight of colloidal silicon dioxide, 0.6% to 0.9% by weight of lubricants and 5.0% to 6.0% by weight of coating agents.

Compositions of present invention may include one or more pharmaceutically acceptable excipients selected from diluents, binders, lubricants, glidants, colorants, coating agents, plasticizers and the like.

Diluents are substances which usually provide bulk to the composition. Diluents which can be used for preparation of Sevelamer hydrochloride compositions as per the invention include, but are not limited to maize starch, microcrystalline cellulose of various grades like Avicel PH 101, 112, 102, pregelatinized starch, mannitol, calcium carbonate, calcium sulfate and the like. Mannitol being the preferred diluent. Diluents may be used in the range of about 5% to about 21% by weight of total composition.

Tablet compositions which uses lactose and dextrose as diluents show discoloration as the tablets turn to yellowish brown colour due to Maillard reaction. As diabetes is the leading cause of end-stage renal disease (ESRD) in many cases, the use of sugars as diluents is avoided. Similarly dibasic calcium phosphate, tribasic calcium phosphate are also avoided since Sevelamer is a phosphate binding polymer and any phosphate containing diluent may compete for phosphate binding activity of Sevelamer.

Considering the end use of the formulation, mannitol is the preferred diluent. On oral administration, mannitol is not absorbed significantly from the gastrointestinal tract. Mannitol is used in direct compression tablet applications or in wet granulation. Granulations containing mannitol have the advantage of being dried easily. Sevelamer hydrochloride being moisture sensitive, mannitol is the preferred diluent as it is not hygroscopic. Various grades of mannitol are available commercially. Preferred grades of mannitol include Pearlitol SD 200 of Roquette, France.

Binders impart cohesiveness to tablet formulation and ensures that the tablet remain intact after compression. Binders which can be used for preparation of Sevelamer hydrochloride compositions as per the invention include, but are not limited to hydroxy propyl methyl cellulose, hydroxy propyl cellulose, hydroxy ethyl cellulose, ethyl cellulose, other cellulose derivatives, maize starch, polyvinylpyrrolidone alone or in combination with polyethylene glycols and the like. Binders may be used in the range of about 3.0% to about 15.0% by weight of total composition. Binder preferred in the practice of the present invention is ethyl cellulose and polyvinyl pyrrolidone with polyethylene glycol 6000.

Different grades of ethyl cellulose having various viscosities are commercially available. Ethyl cellulose of specific grades or blends of different grades may be used to obtain solutions of desired viscosity. Ethyl cellulose having viscosity in the range of 4 cps to 22 cps is used; preferred being ethycellulose with viscosity of about 5 to 15 cps. The preferred grade of ethylcellulose used for Sevelamer: hydrochloride tablets is Ethocel EC-N 7 Pharm manufactured by Dow chemical company. Ethyl cellulose is not metabolized following oral consumption and therefore a non-calorific substance.

Lubricants which can be used for preparation of Sevelamer hydrochloride compositions as per the invention include, but are not limited to stearic acid, calcium stearate, glyceryl monostearate, glyceryl palmitostearate, zinc stearate, magnesium stearate, sodium stearyl fumarate, calcium stearyl fumarate, hydrogenated vegetable oil, mineral oil, polyethylene glycol, sodium lauryl sulphate, and the like. Glidants which can be used include colloidal silicon dioxide, talc and the like. Lubricants and glidants may be used in the range of about 0.1% to about 3.0% by weight of total composition.

According to another embodiment of the invention, the active ingredient Sevelamer hydrochloride used in the composition possess a phosphate binding capacity of about 4.7 mmol/gm to about 6.4 mmol/gm.

Composition prepared by the process as described herein has a loss on drying value of about 3% to about 12%, particularly about 7% to about 9%.

Although the present invention makes use of organic solvents such as isopropyl alcohol for non-aqueous granulation, the organic volatile impurity level in the finished product is quite low and is within the permissible limit. (Limit as per ICH guidelines: 5000 ppm)

Compositions prepared by the novel process as described here withstand the accelerated stability conditions of temperature and relative humidity and maintain their physical and chemical integrity at accelerated conditions of stability.

The present invention further provides use of the compositions of Sevelamer hydrochloride in the control of serum phosphorus in patients suffering from chronic kidney disease (CKD) on hemodialysis.

According to one embodiment, the present invention provides a method for treating a patient suffering from chronic kidney disease (CKD) on hemodialysis comprising administering a therapeutically effective amount of Sevelamer hydrochloride composition.

As used herein, the term "therapeutically effective amount" refers to an amount sufficient to cause an improvement in a clinically significant condition in the patient or even prevent a disease, disorder or condition in a patient.

As used herein, the term "excipient" refers to a pharmaceutically acceptable ingredient that is commonly used in the pharmaceutical technology for preparing granulate and/or solid oral dosage formulations.

As used herein, the term "tablet" is intended to encompass compressed pharmaceutical dosage formulations of all shapes and sizes, whether coated or uncoated.

The present invention is further illustrated by reference to the following examples which does not limit the scope of the invention in any way. It will be apparent to those skilled in the art that many modifications, both to the materials and methods, can be practiced without departing from the purpose and scope of the disclosure.

EXAMPLES

Example 1

Preparation of Polyallylamine Hydrochloride

Allylamine (75 g) was added to hydrochloric acid (134.2 g) by maintaining the temperature 5 to 15° C. The pH was adjusted to 1 to 2 and the solution was stirred for 30 min. The recovery of acidic water at temp below 90° C. was carried out under vacuum to get allylamine hydrochloride salt and the recovery till approx. about 1 volume of water based on input allylamine was distilled out to get thick mass. The reaction mass was cooled to 25 to 35° C. and water was added to get uniform slurry and the reaction mass was heated to 80 to 85° C. VA-086 (9.82 g), an initiator was added in lotwise manner. First lot of VA-086 was added in about 4 hrs at 80 to 85° C. The reaction mixture was maintained at 80 to 85° C. for a further 8 hrs. Second lot of VA-086 was added in about 2 hrs at 80 to 85° C. and the reaction mixture was maintained for a further 10 hrs at 80 to 85° C. The mass was cooled to 40 to 50° C. and the solution was slowly charged to Methanol (1843 ml) (quenching). Two successive washings of methanol (921 ml) were given to the wet cake of polyallylamine hydrochloride by stiffing at 25 to 35° C. for 45 min. The resultant mass was dried at 65 to 70° C. under vacuum.

Example 2

Preparation of Sevelamer Hydrochloride 50 g Poly(allylamine hydrochloride) and 75 ml water were mixed at 25 to 35° C. to get a clear solution. The solution was further cooled to 5 to 15° C. and 13.68 g sodium hydroxide solution in water was added to the reaction mass at 5 to 15° C. and stirred for 30 minutes, 400 ml toluene and 2 g SPAN-85 were added to it at 5 to 15° C. The temperature of the reaction mixture was then raised to 20 to 25° C. and maintained for 15 min. The reaction mixture was filtered to remove any extraneous matter at 25 to 35° C. The temperature of the filtrate was further raised to 55 to 60° C. and maintained for 15 minutes. 4.5 g epichlorohydrin was added at constant temperature of 55 to 60° C. to reaction mixture and maintained for 3 hr at 55 to 60° C. The reaction mixture was cooled to 25 to 35° C. and product was isolated by centrifugation. The wet cake was further sludged with water (3×750 ml) for 45 min at 25 to 50° C. and filtered and dried in FBD at 25 to 90° C.

| | |
|---|---|
| Chloride content | 4.45 meq/g |
| Phosphate binding capacity by IC method | 5.97 mmol/g. |
| Degree of crosslinking | 16.4% |
| Yield | 77.0% w/w |

Example 3

Poly(allylamine hydrochloride) (50 g) and water (75 ml) were mixed at 25 to 35° C. to get a clear solution. The solution was further cooled to 5 to 15° C. and 14.41 g sodium hydroxide solution in water was added to the reaction mass at 5 to 15° C. and stirred for 30 min. Toluene (400 ml) and SPAN-85 (2 g) were added to it at 5 to 15° C. The temperature was then raised to 20 to 25 C and maintained for 15 min. The reaction mixture was filtered to remove any extraneous matter at 25 to 35° C. The temperature of the filtrate was further raised to 55 to 60° C. and maintained for 15 min. Epichlorohydrin (3.395 g) was added to the reaction mixture at constant temperature of 55 to 60° C. and maintained for 3 hr at 55 to 60° C. The reaction mixture was cooled to 25 to 35° C. and product was isolated by centrifugation. The wet cake was further sludged thrice with water (3×750 ml) for 45 min. at 25 to 50° C. and finally with isopropanol (750 ml) followed by filtration and dried in tray driers at 25 to 90° C.

| | |
|---|---|
| Chloride content | 4.8 meq/g. |
| Phosphate binding capacity by IC method | 5.39 mmol/g. |
| Degree of crosslinking | 13.8% |
| Yield | 70.4% w/w |

Example 4

Poly(allylamine hydrochloride) (50 g) and water (75 ml) were mixed at 25 to 35. ° C. to get a clear solution. The solution was further cooled to 5 to 15° C. and 14.41 g sodium hydroxide solution in water was added to the reaction mass at 5 to 15° C. and stirred for 30 min. Toluene (400 ml) and SPAN-85 (2 g) were added to it at 5 to 15° C. The temperature of the reaction mixture was then raised to 20 to 25° C. and maintained for 15 min. The reaction mixture was filtered to remove any extraneous matter at 25 to 35° C. The temperature was further raised to 55 to 60° C. and maintained for 15 min. Epichlorohydrin (4.5 g) was added to the reaction mixture at constant temperature (55 to 60° C.) to reaction mixture and maintained for 3 hr at 55 to 60° C. The reaction mixture was cooled to 25 to 35° C. and product was isolated by centrifugation. The wet cake was further sludged thrice with water (3×750 ml) for 45 min. at 25 to 50° C. and dried in FBD at 25 to 90° C.

| | |
|---|---|
| Chloride content | 4.68 meq/g. |
| Phosphate binding capacity by IC method | 5.51 mmol/g. |
| Degree of crosslinking | 15.38% |
| Yield | 76.0% w/w |

Example 5

Poly(allylamine hydrochloride) (50 g) and water (75 ml) were mixed at 25 to 35° C. to get a clear solution. The solution was further cooled to 5 to 15° C. and 14.41 g sodium hydroxide solution in water was added to the reaction mass at 5 to 15° C. and stirred for 30 min. Toluene (400 ml) and SPAN-85 (2 g) were added to it at 5 to 15° C. The temperature was then raised to 20 to 25° C. and maintained for 15 min. The reaction mixture was filtered to remove any extraneous matter at 25 to 35° C. The temperature of the filtrate was further raised to 55 to 60° C. and maintained for 15 min. epichlorohydrin (4.5 g) was added to the reaction mixture at constant temperature of 55 to 60° C. to reaction mixture and maintained for 3 hr at 55 to 60° C. The reaction mixture was cooled to 25 to 35° C. and product was isolated by centrifugation. The wet cake was further sludged with water (3×750 ml) for 45 min. at 25 to 50° C. and finally with isopropanol (750 ml) followed by filtration. The wet cake is then dried in tray driers at 25 to 90° C.

| | |
|---|---|
| Chloride content | 5.02 meq/g. |
| Phosphate binding capacity by IC method | 5.26 mmol/g. |
| Degree of crosslinking | 15.17% |
| Yield | 75.0% w/w |

Example 6

Co-sifted Sevelamer hydrochloride (1.2 kg) and microcrystalline (Avicel PH 101) (0.28 kg) and mixed in a rapid mixer granulator (RMG). Prepared a solution of polyethylene glycol 6000 (0.135 kg) in purified water and added to the mixture in the RMG. Prepared a solution of povidone K 30 (0.153 kg) in isopropyl alcohol and added to the RMG. Dried the granulated mass. Milled the dried mass using multimill/sifter and further using ball mill to obtain granules which pass through 60# sieve. Lubricated the granules in a conta blender using colloidal silicon dioxide (0.009 kg) and stearic acid (0.009 kg). Compressed the lubricated granules on a conventional tabletting machine to produce 400 mg tablets of Sevelamer hydrochloride. Sevelamer hydrochloride tablets 800 mg was prepared using blend double the weight of that used in 400 mg tablets. Core tablets were further film coated by aqueous process till a weight gain in the range of about 4.0% to about 6.0% is achieved.

Example 7

Mixed mannitol (0.164 kg) and pre-sifted Sevelamer hydrochloride (1.2 kg) in a rapid mixer granulator. Purified water was added to wet the mixture. Prepared the binder solution by dissolving the ethyl cellulose (0.128 kg) in isopropyl alcohol. Binder solution was added to the mixture in RMG which was under fast speed mixing using a peristaltic pump to obtain a cohesive mass. Milled the dried mass using multimill/sifter and further using ball mill to obtain granules which were passed through 60# sieve. Lubricated the granules in a conta blender using colloidal silicon dioxide (0.009 kg) and stearic acid (0.009 kg). Compressed the lubricated granules on a conventional tabletting machine to produce 400 mg tablets of Sevelamer hydrochloride. Sevelamer hydrochloride tablets 800 mg was prepared using blend double the weight of that used in 400 mg tablets. Core tablets were further film coated by aqueous process till a weight gain in the range of about 4.0% to about 6.0% was achieved.

Example 8

Sevelamer hydrochloride 1.2 kg was co-sifted along with Pearlitol SD 200 (about 0.160 kg) through 20 mesh S S Sieve on vibrosifter, and loaded into the rapid mixer granulator and mixed for about 5 minutes. Binder solution prepared by dissolving about 127.5 gm Ethocel N 7 Pharm in 400 gm Isopropyl alcohol was added to the dry mix in the Rapid mixer granulator under fast speed. Addition was done slowly in a continuous stream. After addition of binder further mixing was done at high speed to obtain a cohesive granulated mass. Granulated mass was then air dried without temperature in the Glatt drier or Restch drier and further dried at about 40 to 45 deg C. till loss on drying value not more than 5.0% w/w was achieved. Dried mass was milled, lubricated and compressed according to the procedure described in Example 6. In an alternate method a Planetary mixer was used for the granulation.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for wet granulating sevelamer, the process comprising the steps of:
    a) obtaining sevelamer;
    b) mixing said sevelamer with a granulation liquid,
        i) said granulation liquid comprised of at least one non-aqueous solvent,
        ii) said granulation liquid is further comprised of from 0% to less than about 20% water; and
    c) granulating the sevelamer by wet granulation to produce granulated sevelamer.

2. The process of claim 1, wherein the non-aqueous solvent comprises a short-chain alcohol.

3. The process of claim 2, wherein the non-aqueous solvent comprises ethyl alcohol.

4. The process of claim 2, wherein the non-aqueous solvent comprises isopropyl alcohol.

5. The process of claim 4, wherein said granulation liquid is further comprised of about 5% water.

6. The process of claim 1, wherein the granulation liquid further comprises a binder.

7. The process of claim 6, wherein said binder comprises polyvinylpyrrolidone.

8. The process of claim 1, wherein before the sevelamer is mixed with the granulation liquid, the sevelamer is pre-wet with a wetting solution.

9. The process of claim 8, wherein the wetting solution comprises water.

10. The process of claim 9, wherein the wetting solution further comprises polyethylene glycol.

11. The process of claim 1, wherein the granulated sevelamer has a hydration of not more than about 7% as measured by Karl Fischer analysis.

12. The process of claim 1, wherein the granulated sevelamer exhibits a weight loss on drying of not more than about 15%.

13. The process of claim 2, wherein the granulating is selected from the group consisting of: wet high-shear granulation and wet spray granulation.

14. A composition of matter comprising sevelamer prepared by the process of claim 1.

15. The composition of matter of claim 14, further comprising at least one pharmaceutically-acceptable excipient, said composition in oral tablet form, said tablet providing up to about 1 gram of sevelamer per tablet, said tablet substantially disintegrating in HCl solution within not more than about 3 minutes.

16. In a process of granulating sevelamer, the improvement comprising wet granulation using a granulation liquid comprised of at least one non-aqueous solvent and from 0% to less than about 20% water, whereby the sevelamer may be wet granulated using the granulation liquid.

17. Sevelamer, wet granulated with a granulation liquid comprised of at least one non-aqueous solvent and from 0% to less than about 20% water.

* * * * *